United States Patent
Zweig

(10) Patent No.: US 8,118,991 B2
(45) Date of Patent: *Feb. 21, 2012

(54) APOENZYME REACTIVATION ELECTROCHEMICAL DETECTION METHOD AND ASSAY

(76) Inventor: Stephen Eliot Zweig, Los Gatos, CA (US)

(*) Notice: Subject to any disclaimer, the term of this patent is extended or adjusted under 35 U.S.C. 154(b) by 1033 days.

This patent is subject to a terminal disclaimer.

(21) Appl. No.: 11/656,089

(22) Filed: Jan. 22, 2007

(65) Prior Publication Data

US 2007/0289880 A1    Dec. 20, 2007

Related U.S. Application Data

(63) Continuation-in-part of application No. 11/059,841, filed on Feb. 17, 2005, now Pat. No. 7,166,208, and a continuation-in-part of application No. 10/233,908, filed on Sep. 3, 2002, now Pat. No. 7,291,698, and a continuation-in-part of application No. 10/308,411, filed on Dec. 3, 2002, now abandoned.

(60) Provisional application No. 60/549,691, filed on Mar. 3, 2004, provisional application No. 60/317,023, filed on Sep. 4, 2001, provisional application No. 60/339,916, filed on Dec. 6, 2001, provisional application No. 60/389,679, filed on Jun. 17, 2002.

(51) Int. Cl.
*G01N 27/327* (2006.01)

(52) U.S. Cl. .................... 205/792; 204/403.01

(58) Field of Classification Search ........ 204/403.01–403.15; 205/777.5, 205/778, 792; 600/345
See application file for complete search history.

(56) References Cited

U.S. PATENT DOCUMENTS

| | | | | |
|---|---|---|---|---|
| 3,542,662 A | * | 11/1970 | Hicks et al. | 204/403.09 |
| 3,817,837 A | | 6/1974 | Rubenstein et al. | |
| 4,134,792 A | | 1/1979 | Boguslaski et al. | |
| 4,213,893 A | | 7/1980 | Carrico et al. | |
| 4,238,565 A | | 12/1980 | Hornby et al. | |
| 4,318,983 A | | 3/1982 | Hornby et al. | |
| 4,484,987 A | * | 11/1984 | Gough | 205/778 |
| 4,495,281 A | | 1/1985 | Buckler et al. | |
| 4,545,382 A | | 10/1985 | Higgins et al. | |
| 4,711,245 A | | 12/1987 | Higgins et al. | |
| 4,758,323 A | | 7/1988 | Davis et al. | |
| 5,173,165 A | * | 12/1992 | Schmid et al. | 204/403.1 |

(Continued)

FOREIGN PATENT DOCUMENTS

GB    2188728 A    10/1987

(Continued)

OTHER PUBLICATIONS

Lange et al., "Inhibition of Blood Coagulation Factors by Serine Esterase Inhibitors," FEBS Letters vol. 24, No. 3, pp. 265-268, Aug. 1972.*

(Continued)

*Primary Examiner* — Alex Noguerola

(57) ABSTRACT

The invention discloses a device and method by which dry reagent enzyme based electrochemical biosensors, which are in a relatively mature form due to the extensive amount of development pioneered by the blood glucose monitoring industry, may be simply adapted to perform tests for blood coagulation, enzymatic activity, or immunochemical assays for antigens present in a fluid sample. In particular, the utility of combining apoenzyme based dry reagent electrochemical biosensors with apoenzyme reactivation technology is taught. This combination creates a novel combination test technology capable of detecting a wide range of different analytes, and operating in a wide variety of wet or dry, in vivo or in vitro environments.

20 Claims, 11 Drawing Sheets

U.S. PATENT DOCUMENTS

| | | | |
|---|---|---|---|
| 5,233,025 A * | 8/1993 | Miyazaki et al. | 530/388.9 |
| 5,264,105 A | 11/1993 | Gregg et al. | |
| 5,320,725 A | 6/1994 | Gregg et al. | |
| 5,336,388 A * | 8/1994 | Leader et al. | 204/403.06 |
| 5,418,141 A | 5/1995 | Zweig et al. | |
| 5,580,744 A | 12/1996 | Zweig | |
| 5,708,247 A | 1/1998 | McAleer et al. | |
| 5,727,548 A | 3/1998 | Hill et al. | |
| 5,820,551 A | 10/1998 | Hill et al. | |
| 6,352,630 B1 | 3/2002 | Frenkel et al. | |
| 6,620,310 B1 | 9/2003 | Ohara et al. | |
| 6,673,622 B1 | 1/2004 | Jina | |
| 7,006,858 B2 * | 2/2006 | Silver et al. | 600/345 |

FOREIGN PATENT DOCUMENTS

| | | |
|---|---|---|
| WO | WO 91/16630 | 10/1991 |

OTHER PUBLICATIONS

Heiss et. al. "Dip and read test strips for the determination of trinitrotoluene", Analytica Chimica Acta 396 (1999) 309-316.

Schroeder et. al. "Coupling aminoheyl-FAD to proteins with dimethyladipimidate" Clin. Chim. Sep. 1985; 31(9) 1432-7.

Morris et. al. "Flavin adeinine dinucleotide as a label in homogenous colorimetric immunoassays" Anal Chem 53, 658-665 (1981).

Gavalas et. al. "Biosensors based on enzyme polyelectrolyte complex adsobed into a porous carbon electrode" Biosensors & Bioelectronics 13 (1998) 1205-1211.

Katza et. al. "Glucose oxidase electrodes via reconstitution of the apo-enzyme: tailoring of novel glucose biosensors" Analytica Chima Acta 385 (1999) 45-58.

Vielstich (ed), Mathias et. al. "Diffusion media materials and characterization", Handbook of Fuel Cells—vol. 3 (46), p. 3-9, 2003 John Wiley & Sons, Ltd.

Liu and Wang "Improved design for the glucose biosensor", Food technol. biotechnol. 39 (1) 55-58 (2001).

Hughes et. al. "Allosteric changes in solvent accessibility observed in thrombin uon active site occupation", Biochemistry 2004, 43, 5246-5255.

Szynol et. al. "Bactericidal Effects of a Fusion Protein of Llama Heavy-Chain Antibodies Coupled to Glucose Oxidase on Oral Bacteria", Antimicrobial Agents and Chemotherapy, S.

Yamada et. al. "Mutant Isolation of the *Escherichia coli* Quinoprotein Glucose Dehydrogenase and Analysis of Crucial . . . ", J. Biol. Chem. 273 (34), pp. 22021-22027, 1998.

* cited by examiner

APOENZYME REACTIVATION ELECTROCHEMICAL DETECTION METHOD AND ASSAY

This application is a continuation in part of, and claims the priority benefit of, non-provisional application Ser. No. 11/059,841, filed Feb. 17, 2005 (issuing as U.S. Pat. No. 7,166,208). application Ser. No. 11/059,841 in turn claims the priority benefit of provisional application 60/549,691, "Apoenzyme reactivation electrochemical detection method and assay", filed Mar. 3, 2004. This application is also a continuation in part of, and claims the priority benefit of, U.S. patent application Ser. No. 10/233,908, "Synthetic substrate for high specificity enzymatic assays", filed Sep. 3, 2002 now U.S. Pat. No. 7,291,698. Copending application Ser. No. 10/233,908 in turn claims the priority benefit of provisional application 60/317,023 filed Sep. 4, 2001. This application is also a continuation in part of, and claims the priority benefit of, copending U.S. patent application Ser. No. 10/308,411, "Tethered receptor-ligand reagent and assay", filed Dec. 3, 2002 now abandoned. Copending application Ser. No. 10/308,411 in turn claims the priority benefit of provisional application 60/339,916 (filed Dec. 6, 2001) and 60/389,679 (filed Jun. 17, 2002).

BACKGROUND OF THE INVENTION

1. Field of the Invention

The field of the invention is improved electrochemical diagnostic reagents useful for instrumented tests for coagulation, immunoassays, and other analytes.

2. Description of the Related Art

There is a wide range of chemical entities (test ligands, test analytes) where rapid identification of the presence and relative levels of the entity are highly important. In medicine, it is often critically important to rapidly identify medical analytes such as hormones, drugs, pathogens, and physiological enzymes. In agricultural areas, it is often important to identify trace levels of contaminants or pathogens, such as harmful bacteria, adulterants, or other undesirable contaminants. In environmental studies, it is often important to rapidly identify trace levels of pollutants. For military applications, identification of trace levels of toxic agents is also important.

As a result of this common need for rapid identification of test ligands, various different rapid detection schemes have been devised. These include general-purpose detection methodologies, such as chromatography and mass spectrometry, and more specialized detection methodologies, such as the various diagnostic chemical methodologies that employ test reagents designed to produce detectable signals upon chemical reaction with the test analyte. The present application is focused on this latter type of rapid chemical test methods.

Although complex automated chemical analyzers exist, using liquid chemical reagents, which can rapidly analyze many different types of test ligand, such devices tend to be expensive, delicate, and often require skilled users. As a result, an alternative approach, using premixed reagents stored in a dry form, and reconstituted by the fluid in the test analyte's sample, has become quite popular in recent years. Such tests are referred to generically as "dry reagent tests".

There are two basic categories of dry reagent test. Dry reagent tests that produce a detectable change in the electrochemical potential of an electrode are typically referred to as electrochemical dry reagent tests, and dry reagent tests that produce a detectable optical change in the optical characteristics of the reagent (change in color, change in fluorescence, etc.) are typically referred to by the type of optical change used in the assay (e.g. calorimetric tests, fluorescence tests, etc.).

Due to the high demand for simple blood glucose tests for diabetics, electrochemical dry reagent tests have become increasingly popular in recent years. In contrast to optical dry reagent tests, which require both precise optical measuring equipment, and precise ways to translate the optical signal into a final answer, electrochemical tests usually can function with simpler equipment. The need for a precise optical section is eliminated, and the electrochemical signal generated by the reagent can be converted to a final answer using simple and low cost electronic circuits. As a result, electrochemical blood glucose tests have become a multi-billion dollar a year industry. A wide variety of electrochemical methods have been devised, and due to the high economic activity in this space, the technology is now in a well-developed and mature state.

At present, not all analytes can be measured by electrochemical means. This is because in many cases, simple and practical ways to transduce the chemical signal produced by the test reagent-test analyte reaction over to an electrochemical signal capable of being detected at a test reagent electrode has not been identified. As a result, many useful assays, such as immunochemical assays, enzyme substrate assays, and the like must currently be performed using older optical dry reagent technology. Because, in many cases, this technology is not as fully developed as modern dry reagent electrochemical technology, many of these assays are currently being performed using the older, more expensive, and less reliable optical format. Additionally, the lower volume of many of these assays has made it uneconomic to develop improvements, creating many "orphan" tests that have not improved much beyond the original, previous generation, optical technology.

One example of an "orphan" optical dry reagent technology for immunochemical analytes is the Apoenzyme Reactivation Immunoassay (ARIS). The ARIS concept is based upon the formation of a unique type of hybrid molecule. This hybrid molecule consists of an apoenzyme reactivation factor (also called an enzyme "cofactor", "coenzyme" or "prosthetic group") that is chemically conjugated to a reagent version of the test ligand (antigen) molecule. This conjugation creates a hybrid molecule containing both an enzyme reactivation factor, and a reagent version of the test ligand (antigen) molecule of interest. The ARIS assay also contains reagent antibodies that bind to this hybrid molecule, and an inactive apoenzyme. In the absence of test analytes, the reagent antibodies bind to the hybrid molecule and prevent the molecule's apoenzyme reactivation factor from reactivating the apoenzyme. In the presence of test analytes, however, the test ligands compete for binding to the reagent antibodies, and displace the hybrid molecules away from the reagent antibodies. The now unbound apoenzyme reactivation factors are now free to reactivate the apoenzyme, which in turn produces a colored reaction product. Although, in some cases, such tests can be observed directly by eye without need of automated instrumentation, direct visual methods have limited accuracy. As a result, optical meters more commonly read such tests. However, as previously discussed, optical metering systems tend to be more complex and more susceptible to inaccuracy, relative to electrochemical metering systems, and thus are less economically attractive. Thus methods to translate optical ARIS immunochemical tests to the more mature electrochemical format are desirable.

A second example of "orphan" dry reagent technology is blood coagulation monitoring assays. Here a variety of dry reagent tests exist, including optical tests, and non-standard electrochemical tests. The later works by principles that are substantially different than the more common enzyme based electrochemical biosensors, and thus are not at the same level of technological maturity as most enzyme based electrochemical biosensors.

At present, all coagulation tests are significantly more expensive than electrochemical blood glucose tests, and all require more complex and sophisticated metering systems. Thus methods to translate blood coagulation tests to the more mature and standard enzyme based electrochemical biosensors are also desirable Prior art for electrochemically based prothrombin time assays may be found in U.S. Pat. Nos. 6,066,504; 6,060,323; 6,046,051; 6,673,622 by Jina et. al, U.S. Pat. No. 6,352,630 by Frenkel et. al., and U.S. Pat. No. 6,620,310 by O'hara et. al.

Prior art for thrombin substrate based coagulation assays may be found in U.S. Pat. Nos. 5,580,744 and 5,418,141 by Zweig.

Prior art for dry reagent homogeneous apoenzyme reactivation (ARIS) chemistry and immunochemistry can be found in U.S. Pat. Nos. 3,817,837; 4,134,792; 4,213,893; 4,238,565; 4,318,983; 4,495,281 and others.

Prior art for enzyme based electrochemical biosensors for blood glucose can be found a variety of patents, including many assigned to Genetics International, Medisense, E. Heller, & Company, Therasense, Selfcare, Boehringer Mannheim, and others. These include U.S. Pat. Nos. 4,545,382; 4,711,245; 4,758,323; 5,262,035; 5,262,305; 5,264,105; 5,286,362; 5,312,590; 5,320,725; 5,509,410; 5,628,890; 5,682,884; 5,708,247; 5,727,548; 5,820,551; 5,951,836; 6,134,461 and 6,143,164.

Turner, Miller, and Costa, in UK patent application GB 2188728 A, disclose an apoenzyme reactivated electrode system in which antibodies are conjugated to a prosthetic-group-generating enzyme (aminoacylase). Test antigens act as specific binding pairs to cause the conjugated antibodies to bind to an electrode containing an apoenzyme form of an electrically active enzyme GDH. When test antigens are present, the antibody-aminoacylase-enzyme conjugates specifically bind to the test antigens, and carry the prosthetic-group-generating enzyme aminoacylase to the electrode. The antibody coupled aminoacylase enzyme produces a GDH apoenzyme prosthetic group PQQ. These PQQ apoenzyme prosthetic groups, in turn, bind to the electrode-bound GDH apoenzyme, and change the GDH apoenzyme into an electrically active GDH enzyme. This electrically active GDH enzyme in turn produces an electrical signal that is proportional to the amount of the test antigens in the analyte.

Although 728A teaches one specific method of detecting analytes containing antigens (test antigens), 728A fails to teach general methods for detecting enzymatic activity in test samples (i.e. fails to teach how to detect analytes that are enzymatically active). Rather, 728A simply teaches how to detect binding to an antigen. Although 728A's methods include an enzyme (aminoacylase) labeled antibody, 728A is not detecting aminoacylase enzymatic activity in the sample, nor is 728A detecting any other form of sample enzymatic activity. The aminoacylase enzyme is simply used as an antigen (specific binding) detection tool. The aminoacylase enzyme acts by converting a molecule that is not a GDH prosthetic group into a molecule (PQQ) that is a GDH prosthetic group.

In particular, 728A fails to teach how the activity of analyte enzymes that act to cleave polymeric test substrates by hydrolysis, such as proteases, nucleases, and glycosylases, can be directly detected. This is because such analyte enzymes usually do not create apoenzyme prosthetic groups as a reaction product, which is required by 728A's teaching. Since 728A's "specific binding pair" methods only detect antibody binding, (rather than test enzyme activity), 728A's methods will generally be unable to distinguish between situations where the analyte enzyme is present in an inactive or partially active form, and situations where the analyte enzyme is present in an active form.

Since many useful analytical tests, such as blood coagulation, distinguish between active and inactive forms of analyte enzymes, (where the actual molar concentration of the enzymatic protein itself is unchanged), the specific binding pair methods of 728A are unlikely to be effective for this type of application.

Joseph and Madou, in PCT application WO 91/16630 teach another variant of the binding partner method. This method also relies on directly detecting the concentration of the analyte (e.g. number of moles of antigen or protein present in the sample) by specific binding methods, rather than on detecting the enzymatic activity of the analyte enzymes. Thus, just as previously discussed in more detail for Turner et. al., the methods of Joseph will also generally fail to distinguish between analyte enzymes that are present in an inactive form, and analyte enzymes that are present in an active form. Thus the methods of Joseph and Madou also generally fail to perform for enzymatic tests, such as blood coagulation, that must distinguish between active and inactive forms of analyte enzymes.

Thus there remains a need for simple electrochemical methods that can directly detect relative levels of enzymatic activity in a biological sample of interest, as well as detect analyte (test) antigens of interest.

SUMMARY OF THE INVENTION

The invention discloses methods in which dry reagent electrochemical technology, which is in a relatively mature form due to the extensive amount of development pioneered by the blood glucose monitoring industry, may be simply adapted to perform important hydrolase enzymatic activity tests such as blood coagulation and other biological tests of interest. In another form of the invention, improved immunochemical methods to detect antigens in a biological sample of interest are also discussed.

In the simplest form, the present invention discloses the utility of combining dry reagent electrochemical enzyme based biosensors with apoenzyme reactivation technology to produce a novel diagnostic test platform technology capable of detecting a wide range of analytes, and capable of operating in a dry or wet, in vivo or in vitro, environment.

Here, enzyme based electrochemical biosensors are produced according to essentially normal methods, but with the substitution of an apoenzyme, or otherwise inactivated form of an electrochemical detection enzyme, in place of the normal active form. Thus, for example, in the case where electrochemical glucose tests are used as the basis for the assay, apoglucose oxidase may be used in place of glucose oxidase.

The inactive electrochemical sensor is turned into an analyte specific sensor through the aid of ARIS like enzyme activation factor (cofactor)—test analyte detection moiety conjugates. These conjugates will generally consist of the appropriate enzyme activation factor (for example the FAD prosthetic group in the case of glucose oxidase), typically linked to a test-analyte detection moiety by a covalent link or high affinity non-covalent link.

In addition to the enzyme activation factor (cofactor), the test analyte detection moiety has two other parts; an analyte detector part (region) and a blocker part (or region). The moiety's "detector" region is the part of the molecule that interacts specifically with the test ligand, and has a state that is altered as a result of interacting with the test ligand. For example, if the test ligand is a hydrolase enzyme such as a protease, the detector region may be a hydrolase substrate, such as a protease substrate peptide, that is cleaved by the hydrolase enzyme. For an immunoassay, the detector region is a reagent antigen-antibody pair that is disrupted by the presence of antigenic test ligands.

The blocker part of the analyte detection moiety is an entity that, in the absence of interactions between the moiety's detector region and the test ligand, acts to prevent the enzyme activation factor from binding to the inactivated enzyme (apoenzyme) on the sensing electrode. For example, in the case of a protease substrate assay, the "blocker" region may consist of a larger molecule that acts to sterically prevent the enzyme activation factor part of the conjugate from binding to the inactivated enzyme on the electrode. In the case of an immunochemical assay, the "blocker" region may be an antibody that binds to the conjugate's antigenic "detector" region, and acts to sterically block the enzyme activation factor from binding to the inactivated electrode enzyme. In some cases, the blocker regions may also act to physically separate the enzyme cofactors or prosthetic groups from the region of the assay that contains the apoenzymes. For example, in the case of an immunochemical assay, the "blocker" antibody may be bound to a membrane, bead, or other structure that is close to, but physically distinct from, the region of the assay where the apoenzyme is located.

Most electrochemically active enzymes require cofactors to operate, and the present invention can work with nearly all of the many different varieties of known enzyme electrode designs, including designs with direct electron transfer between the enzyme and the electrode, electron transfer mediated by diffusion mediators, electron transfer by dissolved enzymes at mediator functionalized electrodes, polymer and inorganic matrix immobilized enzymes contacted by co-immobilized mediators, electrochemical transfer by interprotein electron transfer, and other means commonly used to produce enzyme electrodes (see Katz et. al., Mediated electron-transfer between redox-enzymes and electrode supports. In: *Encyclopedia of Electrochemistry, Vol. 9: Bioelectrochemistry*, G. S. Wilson, (Ed.), A. J. Bard, M. Stratmann (Editors-in-Chief), Wiley-VCH GmbH, Weinheim, Germany 2002, Chapter 17, pp. 559-626), In an alternative configuration of the present invention, unbound (not complexed with their corresponding apoenzyme) prosthetic groups (such as FAD) may be electronically "wired" to electrodes via a molecular link that enables electron transport. Again using apoglucose oxidase as an example, in this alternative configuration, the apoglucose oxidase molecules may themselves be conjugated to an ARIS like test analyte detection moiety, which is in turn bound to a blocker entity. In this case, apoglucose oxidase will be released from this blocker by the action of the test analyte. The liberated apoglucose oxidase can then bind to the wired unbound FAD groups, reassociate, and then start generating an electrical signal that increases in response to higher levels of the test analyte. Thus, for an immunoassay, an antigenic test analyte can displace a conjugate of apoglucose-oxidase and reagent-antigen from a bead or blocker bound antibody, allowing the apoglucose oxidase to diffuse over to the unbound "wired" FAD group, reassociate, and generate an electrical signal. Similarly for a coagulation assay, a coagulation protease can cleave an apoglucose oxidase-protease substrate link to a bead or blocker surface, again enabling the apoglucose oxidase to diffuse over to the "wired" unbound FAD group, reassociate and again generate an electrical signal.

In yet another embodiment of the invention, the electrochemically active enzyme may contain its cofactor or prosthetic group; yet still require an allosteric enzyme-regulating agent (which is not a classical cofactor or prosthetic group) for activation. In this later embodiment, the test analyte will act to release the allosteric regulating molecule from a bound state, and this unbound allosteric regulator will then activate the electrochemically active enzyme. Such allosteric enzyme regulation may be done by binding of an allosteric moiety, by covalent enzyme modification (e.g. phosphorylation, acetylation, myristoylation, ADP-ribosylation, farnesylation, γ-carboxylation, sulfaction, ubiquinitination, glycosylation, etc.), by proteolytic cleavage, or other posttranslational modification.

DETAILED DESCRIPTION OF THE INVENTION

Reference to other US patent applications: The disclosures of application Ser. Nos. 11/059,841; 60/549,691; 10/233,908; 10/308,411 and 10/885,429 are incorporated herein by reference.

Nomenclature: a "test substrate" is a substrate that is cleaved by an analyte (test) hydrolase enzyme to liberate an apoenzyme prosthetic group. An "amplification substrate" is a substrate that is used by the reactivated apoenzyme (electrically active enzyme) to produce an electrical signal. The amplification substrate, in conjunction with the reactivated apoenzyme, acts to amplify the signal generated by the cleavage of the test substrate, and changes this signal into an electrochemical signal.

Figure 1:
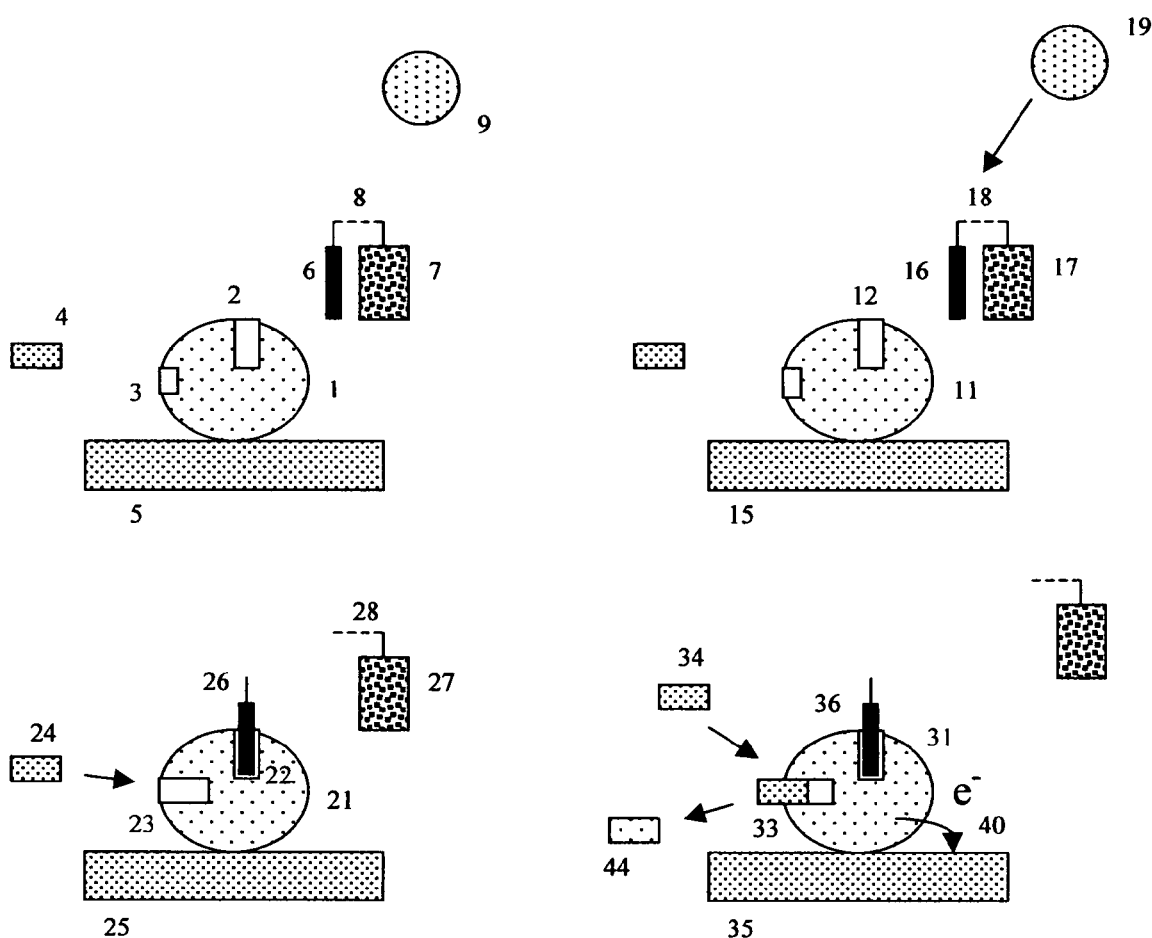
FIG. 1 shows the chemical reactions of the apoenzyme electrochemical detection system detecting an analyte that is a protease (proteolytic enzyme).

FIG. 1 shows an example of an apoenzyme electrochemical protease assay, used to detect test enzymes (analyte enzymes), such as proteases, that act to cleave a larger polymeric test substrate (such as protein) into smaller subunits. Here the apoenzyme (1), which may be the apoenzyme form of glucose oxidase, or other enzyme, is mounted or otherwise associated with the surface of electrode (5). Apoenzyme (1) contains a binding site for a prosthetic group (2), which, in the case of a glucose oxidase apoenzyme would be a FAD (flavin adenine dinucleotide) group. Apoenzyme (1) additionally contains a substrate-binding site (3) for enzyme substrate (4). In this example, enzyme substrate (4) would be glucose. Note that in the apoenzyme form of the enzyme, substrate-binding site (3) will be in an inactive conformation.

In this example, the device additionally contains the FAD apoenzyme prosthetic group (6) complexed to a molecule or surface (7) by way of protease test substrate peptide (8). Surface (7) makes it sterically infeasible for prosthetic group (6) to bind to the apoenzyme prosthetic group binding site (2). Protease test substrate peptide (8) contains a peptide region that serves as a substrate to a proteolytic test enzyme of interest (9), and is cleaved by proteolytic enzyme (9). In the case of a coagulation assay, (such as a prothrombin time assay) the test or analyte enzyme (9) may be thrombin, which is produced by the reaction of thromboplastin in the reagent (not shown) with the various clotting factors present in a patient sample.

As the test reaction progresses, proteolytic test or analyte enzyme (19) cleaves the test substrate peptide (18) that binds the prosthetic group (16) to the molecule or surface (17) that prevents the prosthetic group (16) from binding to enzyme prosthetic group binding site (12). As a result of this proteolytic cleavage, prosthetic group (16) now is liberated for binding. Note that in contrast to the methods of Turner (who uses the reagent enzyme aminoacylase to generate prosthetic groups during the course of the assay), in the present art, prosthetic group (16) is present before the assay begins, and particularly before test or analyte enzyme (19) is introduced to the system. Test or analyte enzyme (19) acts to liberate prosthetic group (16) from a bound state to a more freely migrating state by the hydrolytic (cleaving) activity of test or analyte enzyme (19). However test enzyme (19) does not create the prosthetic group. This distinction is critical. There are only a small number of enzymes (most such as aminoacylase, being medically non-relevant), which act to create prosthetic groups (e.g. PQQ) for other enzymes (e.g. GDH). By contrast there are a very large number of medically important enzymes that act to cleave larger polymeric substrates into smaller subunits. Thus by utilizing a previously generated but bound prosthetic group, the methods of the present disclosure may be extended to encompass a much larger number of medically useful and important test enzymes.

As a result of this liberation, prosthetic group (26) binds to prosthetic group binding site (22), and converts the inactive apoenzyme (of an electrically active enzyme) to an active holoenzyme (enzyme). As a result of this activation, the active site of this electrically active enzyme (23) changes conformation, and becomes capable of performing enzymatic activity. In particular, it is now capable of enzymatically altering enzyme amplification substrate (24), in a reaction that produces a detectable electrochemical change.

As a result of these changes, electrically active enzyme (31) activated by the binding of prosthetic group (36) is able to amplify the signal produced by the proteolytic cleavage of peptide analyte test substrate (18) many times. The electrochemically active enzyme converts large amounts of its amplification substrate from substrate (34) to product (44) by way of active site (33). In the process, enzyme (31) is the source or sink for a large number of electrons (40), which can, in turn, react with electrode (35) and produce a detectable electrochemical signal. In the case where enzyme (31) is glucose oxidase, the amplification substrate (34) is glucose, the product (44) is gluconolactone, and the prosthetic group (36) is flavin-adenine dinucleotide (FAD).

In addition to protease enzymes, the scheme shown in FIG. 1 is generally applicable for detecting a broad range of other enzymes in the hydrolase class. To briefly review, hydrolases are enzymes that catalyze the hydrolysis of chemical bonds. By doing so, hydrolases act to "break" the chemical bonds that bind larger molecules together, resulting in the formation of two smaller reaction products. The general form for a hydrolase enzyme reaction is:

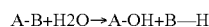

$$A\text{-}B + H2O \rightarrow A\text{-}OH + B\text{---}H$$

The class of hydrolase enzymes (Class EC-3) contains many different enzymes that can cleave a larger molecule into two smaller fragments. Some of the more prominent members of the hydrolase EC-3 class includes proteases, and also includes other enzymes such as esterases (EC-3.1), which encompass nucleic acid cleaving enzymes such as restriction enzymes; glycosylases (EC-3.2), which encompasses carbohydrate-cleaving enzymes such as amylase; and peptidases (another term for protease) (EC-3.4), which, encompasses proteases that cleave peptide bonds.

By contrast aminoacylase, previously used by Turner to generate PQQ prosthetic groups, is in the different EC-3.5 (3.5.1.14) class.

Thus, as can be seen from FIG. 1, if the test substrate (8), (18), is a nucleic acid (such as DNA) and the analyte or test enzyme (9), (19) is an EC-3.1 restriction enzyme, the restriction test enzyme will act to cleave the link (cleave the test substrate) and separate the prosthetic group (6), (16), from the blocking group or surface (7), (17), liberating the prosthetic group, thus reactivating apoenzyme (21), (31) and producing a detectable signal. Similarly, if the test substrate (8), (18) is a long chain carbohydrate such as glycogen, and the analyte enzyme (9), (19) is a glycogen cleaving enzyme such as amylase, the amylase will also act to cleave the link and separate the prosthetic group (6), (16) from the blocking group or surface (7), (17), again liberating the prosthetic group, reactivating apoenzyme (21), (31), and producing a detectable signal. For the proposes of this discussion, although the protease member (EC 3.4) of the broader hydrolase EC-3 class are often used as a specific example, the disclosure should be construed as teaching methods generally applicable those members of the broader EC-3 hydrolase class that cleave larger polymeric test enzyme substrates into one or more smaller subunits. In particular, the specific teaching of FIGS. 3, 5, and 7 should be read and interpreted in view of the more general hydrolase disclosure for FIG. 1, discussed above.

Apoenzyme Cofactor Discussion:

Apoenzymes or inactive enzymes may be reactivated (acquire catalytic activity) by many different cofactors, coenzymes, or prosthetic groups. These cofactors vary according to the enzyme in question. As previously discussed, apoglucose oxidase, used her as an example, is activated by the prosthetic group FAD. Other apoenzymes and cofactor requiring enzymes suitable for the present invention require other cofactor molecules. Some of the other cofactors required to produce catalytic activity in other enzymes include 6-hydroxyDOPA, Ammonia, Ascorbate, ATP, Biotin, Cadmium, Calcium, Cobalamin, Cobalt, Coenzyme-A, Copper, Dipyrromethane, Dithiothreitol, F420, FAD, Flavin, Flavoprotein, FMN, Glutathione, Heme, Heme thiolate, Iron, Iron-molybdenum, Iron-sulfur, Lipoyl groups, Magnesium, Manganese, Molybdenum, NAD, NAD(P)H, Nickel, Potassium, PQQ, Protoheme IX, Pterin, Pyridoxal-phosphate, Pyruvate, Reduced flavin, Selenium, Siroheme, Tetrahydropteridine, Thiamine pyrophosphate, Vanadium. and Zinc.

Apoenzymes and cofactors or prosthetic groups suitable for the present reaction generally are chosen using the following criteria:

1: The apoenzyme must be stable enough to be stored for the desired storage time of the assay. Typically this will requite that the apoenzyme be stable for months or even years.

2: The cofactor or prosthetic group that activates the apoenzyme should be not normally found in the test sample in question (since this can cause interference). One way to avoid such interference is to look for apoenzymes and cofactors from biologically very distant organisms (relative to the organism being tested), as evolutionarily distant organisms are more likely to have evolved unique apoenzyme-prosthetic group/cofactor combinations.

3: The apoenzyme should be able to rapidly (ideally a few seconds or less) combine with its cofactor to produce an electrically active enzyme in the chemical environment of the assay (i.e. not require exotic chemical conditions that are incompatible with the detection of the analyte in question).

Electrically active enzyme substrate (amplification substrate) discussion:

The substrate (amplification substrate) for the electrically active enzyme is different from the cleavable test substrate for the test or analyte enzyme (analyte substrate) previously discussed. In contrast to the cleavable analyte test substrate, which serves to initially detect the presence or absence of test enzyme activity, the amplification substrate for the electrically active enzyme (the active form of the apoenzyme) is a molecule that is used to create a large electrical signal after the test or analyte enzyme cleaves the analyte-substrate.

The amplification substrate for the electrode (electrochemically active) enzyme may either be incorporated into the reagent itself, or else can be a normal component of the liquid sample. As an example, glucose is the substrate for glucose oxidase. A common diagnostic fluid is blood, which normally contains glucose, in addition to other analytes of interest. In this case, when the electrode enzyme is the apo form of glucose oxidase, and the reactivated enzyme is glucose oxidase, the amplification substrate is glucose, and glucose amplification substrate may be provided as part of the test reagents, or alternatively may be obtained from the glucose normally present in the blood sample.

Thus, although the amplification substrate for the electrochemically active enzyme will usually be incorporated as part of the test reagents, when this amplification substrate is expected to be normally present in the liquid sample, this amplification substrate may be omitted.

Electron Transport Mediator Discussion:

After the apoenzyme or inactive electrochemical enzyme has been converted to an active form by interacting with the enzyme activation factor portion (such as a prosthetic group) of the test analyte detection moiety conjugates, various means may be used to transfer electrons produced by the catalytic activity of the newly reactivated electrochemical enzyme back to a reference electrode.

In one scheme, both the newly reactivated enzyme, and at least some of the means to transport electrons from the enzyme to the electrode surface, both exist in a non-electrode bound form. Here, electron transport occurs by way of a diffusible electron transport mediator, such as hydrogen peroxide ($H_2O_2$). This electron transport mediator, produced by the newly reactivated enzyme, may diffuse to a transducer enzyme, such as horseradish peroxidase (HRP). The HRP may in turn be bound to an electrode surface, either by a covalent linkage, or by a non-covalent interaction. HRP will in turn react with the diffusible mediator, and produce electrons, which in turn will transfer to the electrode, where the reaction may be detected. A number of possible transducer enzymes exist, including HRP (previously mentioned), cytochrome c, and others. Typically the active electron transport center of the transducer enzyme is relatively exposed to the outside environment, and thus can easily exchange electrons with electrode surfaces.

In some cases, the mediator molecule may be a soluble artificial electron transport mediator, such as (S)— and (R)— N,N-dimethyl-1-ferrocenyl-ethylamine, methylene blue, and others that can transport electrons directly from the reactivated enzyme to the electrode surface without need of an intermediate transducer enzyme.

In a second scheme, the newly reactivated enzyme is still free to diffuse in solution, but all other parts of the electron transport mediator system are bound to the electrode surface.

Here, the mediator molecule may be an electrode bound artificial electron transport mediator, such as (R)- and (S)-2-Methylferrocene carboxylic acid bound to a silver electrode. Other mediator molecules that can be covalently bound to electrodes include $C_{60}$ (buckyballs), microperoxidase (the active site of cytochrome c), porphyrin rings, and other molecular entities.

In a third scheme, the apoenzyme or inactive form of the electrochemical enzyme is chemically modified by binding an electron transport mediator to the surface of the apoenzyme. For example, ferrocene electron transport mediator molecules may be linked to lysine amino acid residues on the apoenzyme via amide bonds. When reactivated by the enzyme activation factor portion of the test analyte detection moiety, the mediator-modified enzyme may then diffuse and transport electrons directly to electrode surfaces.

In a fourth scheme, the apoenzyme or inactive electrochemical enzyme itself is bound to the electrode surface, and the mediator is also bound to the electrode surface. Here the enzyme may be imbedded in a conducting polymer matrix, such as ferrocene-containing pyrrole derivatives, hydrophilic epoxy cements derivitized to contain electrically conducting pyridinium-N-ethylamine polycationic domains, copolymers of allylamine and ferrocene-functionalized acrylic acid, silicon alkoxide sol-gel matrices doped with electron-transfer mediators, and the like. Since the electrochemical enzyme is immobilized onto the electrode surface, these later schemes have the advantage of often being very stable and very sensitive.

In general, any electron transport scheme will work, with the possible exception of schemes that attempt to link the electrochemical enzyme to the electrode surface by way of the same enzyme activation factor (or prosthetic group) needed to activate the electrochemical enzyme in the first place. For example, attempts to produce this type of assay by linking apoglucose oxidase to electrode surfaces by way of electrode bound FAD molecules, while also attempting to use FAD as the enzyme activation factor portion of the test analyte detection moiety, will tend to encounter problems for in some test configurations. The apoglucose oxidase has previously been converted to active glucose oxidase during the initial linking process. As a result, addition of excess FAD groups from the test analyte detection moieties will have no effect on enzyme activity. However for test configurations that rely upon the migration of apoglucose oxidase or an electrochemical hybrid antibody to a bound prosthetic group, such linked prosthetic group techniques may actually be preferred.

Figure 2:
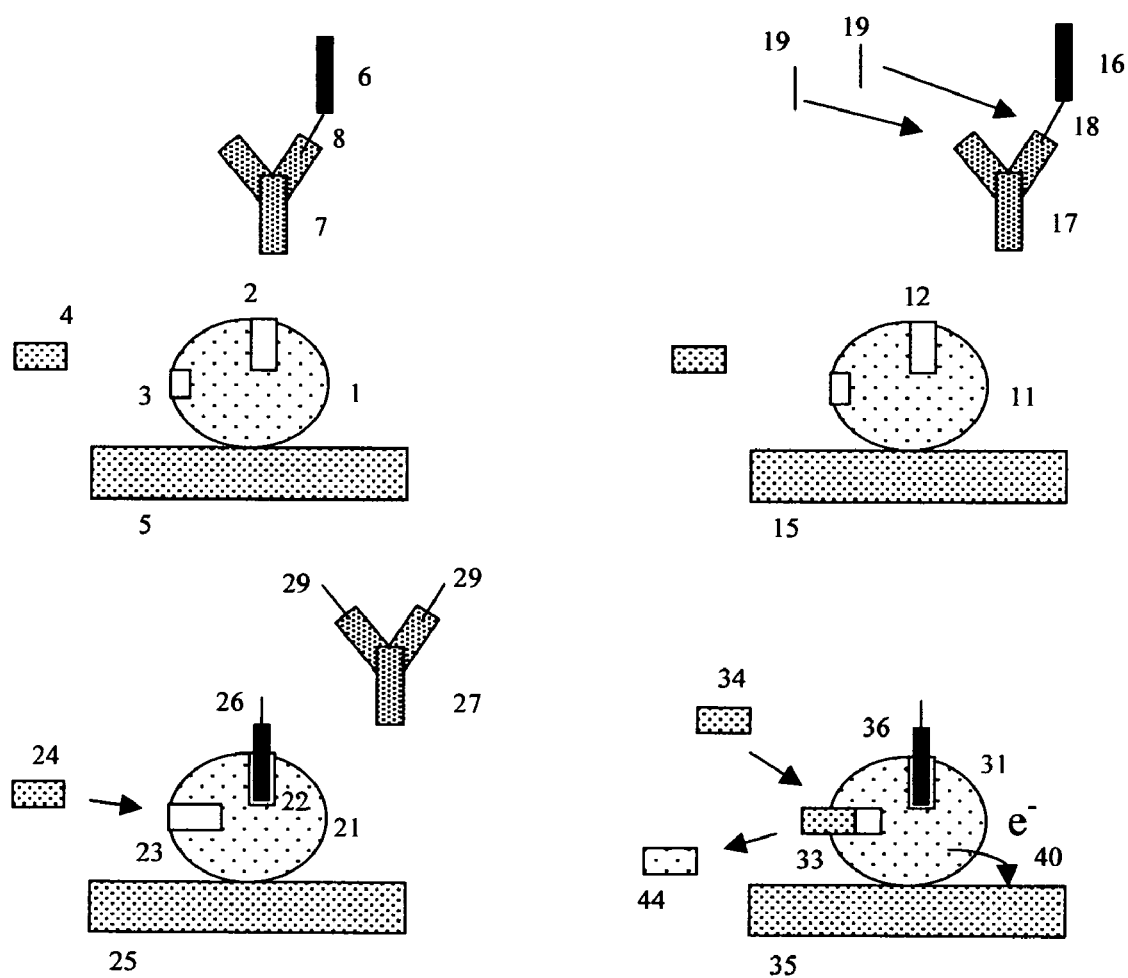
FIG. 2 shows the chemical reactions of the apoenzyme electrochemical detection system functioning as an immunochemical assay for an immunologically reactive analyte.

FIG. 2 shows an example of an apoenzyme electrochemical immunochemical assay. Here, as before, the electrochemical apoenzyme (1), which may be the apoenzyme form of glucose oxidase, or other enzyme, is mounted or otherwise associated with the surface of electrode (5). Apoenzyme (1) contains a binding site for a prosthetic group (2), which, in the case of a glucose oxidase apoenzyme would be a FAD group. Apoenzyme (1) additionally contains a substrate-binding site (3) for amplification enzyme substrate (4). Again in this example, enzyme substrate (4) would be glucose. Note that in the apoenzyme form of the enzyme, substrate-binding site (3) will be in an inactive conformation.

In this example, the device additionally contains an ARIS type hybrid molecule consisting of apoenzyme prosthetic group (6) coupled to reagent ligand (antigen) (8). This hybrid molecule is in turn bound to antibody (7). The coupling between the prosthetic group (6) and the reagent ligand (antigen) (8) will normally be by either a covalent bond, or a tight non-covalent bond such as an avidin-biotin linkage. The binding of the prosthetic group to the antibody (by way of reagent antigen (8)) makes it sterically infeasible for prosthetic group (6) to bind to the electrochemical apoenzyme prosthetic group binding site (2).

As the test reaction progresses, excess unbound ligands (antigens) present in the test sample (19) compete with the prosthetic group bound reagent ligand (antigen) (18) for binding to antibody (17). This displaces prosthetic group (16), and makes it available for binding to the prosthetic group binding region (12) of apoenzyme (11).

As a result of this liberation, prosthetic group (26) binds to prosthetic group binding site (22), and converts the inactive apoenzyme to an active enzyme. As a result of this activation, the active site of this enzyme (23) changes conformation, and becomes capable of performing enzymatic activity. In particular, it is now capable of enzymatically altering amplification enzyme substrate (24), in a reaction that produces a detectable electrochemical change.

As a result of these changes, electrochemical enzyme (31) activated by the binding of prosthetic group (36) is able to amplify the signal produced by binding of the sample test ligand (antigen) (19, 29) to the antibody (17, 27) many times. The enzyme converts large amounts of amplification substrate from substrate (34) to product (44) by way of active site (33). In the process, enzyme (31) is the source or sink for a large number of electrons (40), which can, in turn, react with electrode (35) and produce a detectable electrochemical signal. Again, in the case where electrochemical enzyme (31) is glucose oxidase, the amplification substrate (34) is glucose, the product (44) is gluconolactone, and the prosthetic group (36) is flavin-adenine dinucleotide (FAD).

Application to Prothrombin Time Tests and Other Blood Coagulation Assays:

Prothrombin time tests: Certain types of patients, such as patients with artificial heart valves, atrial fibrillation, and other cardiovascular disorders have a heightened risk of blood clot formation, which can lead to stroke or pulmonary embolism. To treat these disorders, physicians commonly prescribe oral anticoagulants, such as warfarin. Oral anticoagulants diminish the ability of the bodies natural "extrinsic pathway" of proteolytic enzymes to produce a clot. This pathway consists of several proteolytic enzymes, including factor VII, factor X, and thrombin. In the body, the extrinsic coagulation pathway is triggered when thromboplastin, a natural membrane-tissue factor component of the blood vessel's endothelial lining, is released from the interior of the cells due to cellular damage. The thromboplastin activates factor VII, which in turn activates factor X, which in turn activates thrombin, which in turn converts fibrinogen to fibrin, forming a clot. In the normal state, this system acts to prevent bleeding due to minor wounds and other minor damage, but in under pathological conditions (such as heart or circulatory system disorders) can cause a lethal blood clot.

To prevent dangerous blood clots, physicians attempt to diminish the activity of this pathway with oral anticoagulants. It is important to not completely block this pathway, however, since doing so can put the patient at high risk of a lethal bleeding event. To determine if a proper amount of anticoagulant has been administered, the functional capability of the extrinsic coagulation pathway is tested. Since the pathway ends up converting an inactive enzyme, prothrombin, to an active enzyme, thrombin, it is called a prothrombin time test.

In a prothrombin time test, a sample of blood, preferably a single drop of blood from a fingerstick, is exposed to the coagulation initiating chemical, thromboplastin, at a controlled temperature, such as 37° C. The time elapsed between the initial exposure to thromboplastin, and the subsequent development of thrombin activity, is the "prothrombin time" of the sample, and lets the physician know if an adequate dose of anticoagulants has been given. If the prothrombin time is too short, the patient has not been adequately anticoagulated. If the prothrombin time is too long, the patent has been overly anticoagulated.

The electrochemical apoenzyme reactivation technology of the present disclosure can be readily adapted to produce a prothrombin time test, other type of blood coagulation test, or other type of protease or hydrolytic enzyme cascade test. To do this, two things are required. The first is that the test device must contain a detector region that is sensitive to the progress of the coagulation pathway. Usually this detection moiety will be a protease substrate, such as the thrombin test substrate peptide Gly-Pro-Arg (or other test substrate peptide, which may include spacer peptides on either end to facilitate the reaction), which is cleaved by active thrombin. In the case where the basic electrochemical detector is based upon apoglucose oxidase, the test analyte detection moiety conjugate may consist of: FAD-(thrombin substrate)-anchor. Here the "anchor" group (blocking group) is chosen for its ability (prior to test substrate cleavage by the coagulation protease) to sterically hinder the reassociation between the FAD group on the conjugate, and the FAD binding region on apoglucose oxidase.

The blocking group or "anchor group" can be many different things. It can simply be a larger soluble and relatively inert protein, such as an antibody or albumin protein, chosen solely on its ability to serve as a steric blocking group, and not otherwise interfere with the assay. Alternatively, the anchor can be a bead, membrane, or region on the electrode surface, spatially separated from the apoglucose oxidase molecule, so that the FAD prosthetic group is kept separate from apoglucose oxidase in the absence of thrombin proteolytic cleavage of the protease peptide test substrate.

In the case of a prothrombin time test, the second thing that is required is that the test should contain thromboplastin. This is required in order to trigger the start of the coagulation cascade. If use with fresh whole blood is desired, no other components need be present. If use with citrate anticoagulated venous blood or plasma is desired, extra calcium to overcome the effects of the citrate anticoagulation, and optionally a buffer to maintain pH control, may also be used.

Thus the minimal list of materials needed to produce an apoenzyme based electrochemical prothrombin time assay is as follows:

Apoglucose oxidase (or other inactive enzyme that produces an electrochemical change upon reaction)
FAD-[thrombin substrate]-anchor (test substrate)
Glucose (needed as an amplification enzyme substrate for glucose oxidase)
Electron transport mediator
Optional polymer or crosslinker to hold apoglucose oxidase and the electron transport mediator onto the electrode surface
Electrode and reference electrode
Thromboplastin
Optional calcium (usually present as a few mM $CaCl_2$)
Optional buffer (used to control the pH of the reaction).

The components will typically be packaged in the form of a standard point-of-care dry reagent electrochemical test strip. In order to allow instant rehydration of the thromboplastin, and minimal distortion of the coagulation reaction, it may be desirable to position the thromboplastin in the test device so that the sample contacts the thromboplastin slightly before (ahead of when) the sample contacts the electrodes.

Figure 3:
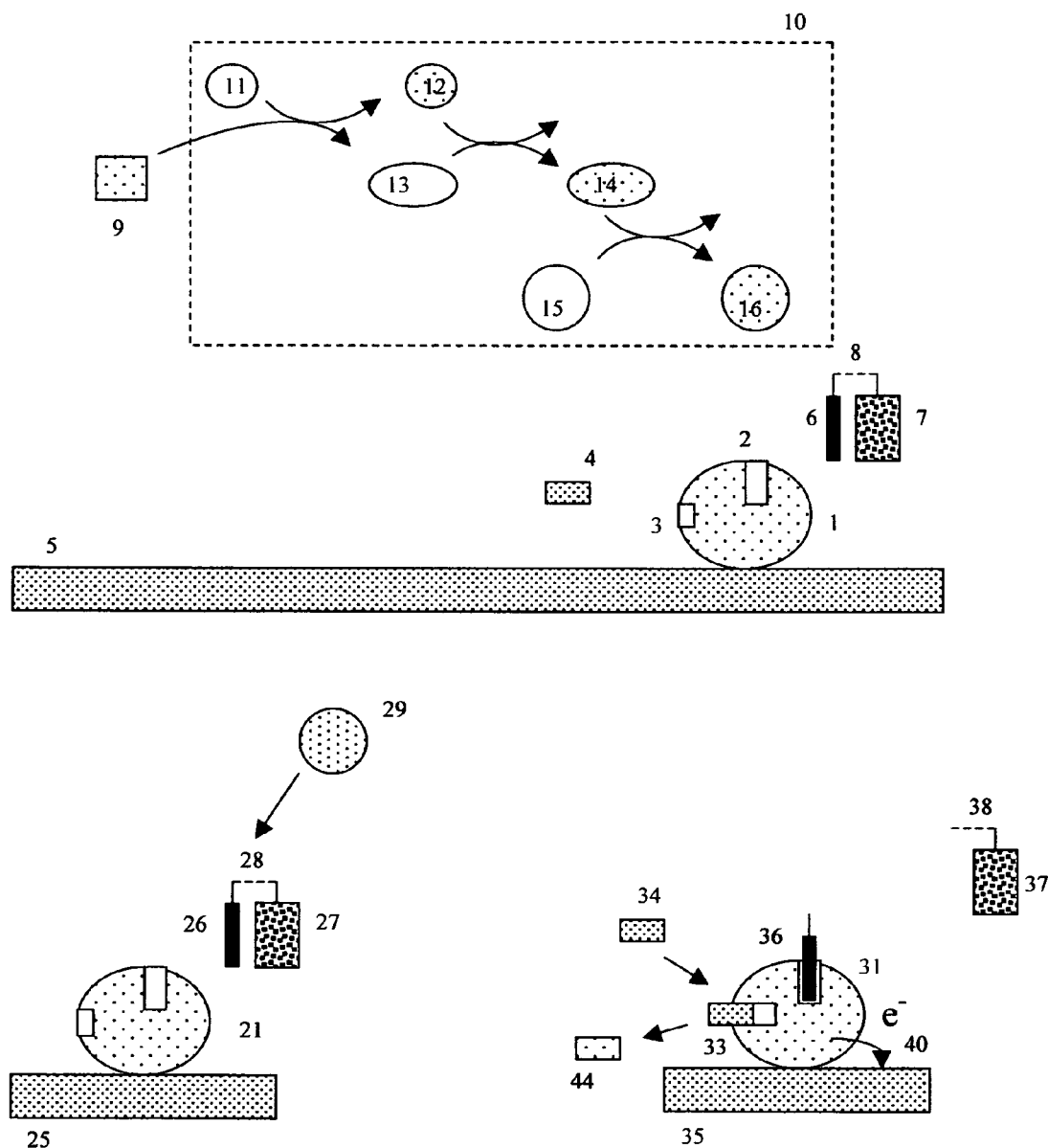
FIG. 3 shows the chemical reactions of the apoenzyme electrochemical detection system functioning as a prothrombin time assay for blood coagulation.

FIG. 3 shows an example of a prothrombin time test adapted to the present format.

Here the inactive enzyme (apoenzyme) (1) containing a cofactor or prosthetic group binding site (2) and amplification substrate binding site (3) for enzyme amplification substrate (4) is mounted or otherwise associated with the surface of electrode (5).

In this example, the device additionally contains the apoenzyme prosthetic group (6) complexed to a molecule or surface (7) that makes it sterically infeasible for prosthetic group (6) to bind to the apoenzyme prosthetic group binding site (2). In this example, prosthetic group (6) is bound to molecule or surface (7) by way of a peptide (8) that contains a region that serves as a peptide test substrate to a coagulation factor proteolytic enzyme. In this example, the peptide (8) is a thrombin test substrate.

The test device additionally contains thromboplastin (9), which is used to initiate the extrinsic coagulation pathway that leads to blood coagulation.

In use, a patient test sample (10) (such as blood or plasma) is applied to the test device. The test sample will normally contain unknown levels of a number of different proteases and other factors involved in the extrinsic coagulation pathway, including unknown levels of Factor VII (11), Factor X (13), prothrombin (15), and typically other factors such as fibrinogen (not shown).

When the thromboplastin present in the test device (9) contacts the Factor VII in the patient sample (11), Factor VII is converted to an activated form (12). The activated form of factor VII (12) in turn converts the inactive form of Factor X (13) to the active form (14). Activated Factor X (14) then converts prothrombin (15) to thrombin (16). Thrombin (16) is a highly active protease enzyme.

The next steps of the reaction are shown in 21, 24, 25, 26, 27, 28 and 29. Here thrombin (29) starts to cleave the protease test substrate region (28) on the test analyte detection moiety conjugate (26, 27, 28). As previous, the apoenzyme or otherwise inactive enzyme (21) remains associated with electrode surface (25), and is not yet reacting with its amplification enzyme substrate (24).

The final stages of the reaction are shown in 31, 33, 34, 35, 36, 37, 38, and 44. Here, as a result of the action of thrombin (29) in the previous flame, the thrombin substrate test peptide (28) has broken (been cleaved). The residual groups from the test analyte detection moiety conjugate, namely the blocking group (37), and the cleaved region of the protease test substrate (38) no longer block the binding of the enzyme reactivation group (36) to the electrochemical enzyme. The liberated enzyme prosthetic group (or other enzyme reactivation factor) (36) can now bind to the prosthetic group region of apoenzyme (31). This activates the apoenzyme (31), thus restoring the enzymatic activity of the enzyme. The newly reactivated enzyme is now able to convert its enzyme amplification substrate (34), by way of the enzyme's active site (33), producing a reacted amplification substrate (44), and electrons (40). The electrons (40) are transferred to electrode (35) by one of the previously discussed electron transport mediators (not shown).

It should be apparent that by changing the chemistry of the specific coagulation pathway initiator and/or test substrate peptide, other coagulation pathways and coagulation tests may be devised using the same principles discussed above for prothrombin time tests. For example, the intrinsic coagulation pathway can be activated using the appropriate initiator, and an Activated Clotting Time (ACT) test for intrinsic coagulation pathway inhibitors, such as heparin, can also be created. Alternatively by using other test substrates and enzyme cascade activation factors, a broad variety of useful enzymes and enzymatic pathways may be detected.

One drawback of using a soluble antibody system (shown in FIG. 2), or a soluble enzyme substrate blocking molecule system (shown in FIG. 1) is that if the enzyme activation prosthetic group is not tightly held next to the surface of the antibody (FIG. 2 (7)), or tightly held next to the surface of the steric blocking group anchor molecule (FIG. 1 (17)), an unwanted high background signal can result. This background signal can be caused when, due to random Brownian motion, the sterically blocked prosthetic groups bump up against the apoenzyme with enough force to knock the prosthetic group free from the steric blocking group or antibody, causing some background apoenzyme reactivation in the absence of suitable test ligands.

As previously discussed, this background can be reduced by binding the apoenzyme and the test analyte detection moiety conjugates to bead, membrane, or electrode surface "anchor groups" that physically separate the enzyme activation cofactors or prosthetic groups from the electrochemical apoenzymes. These anchor group separation concepts are discussed in more detail in FIGS. 4 and 5.

Figure 4:
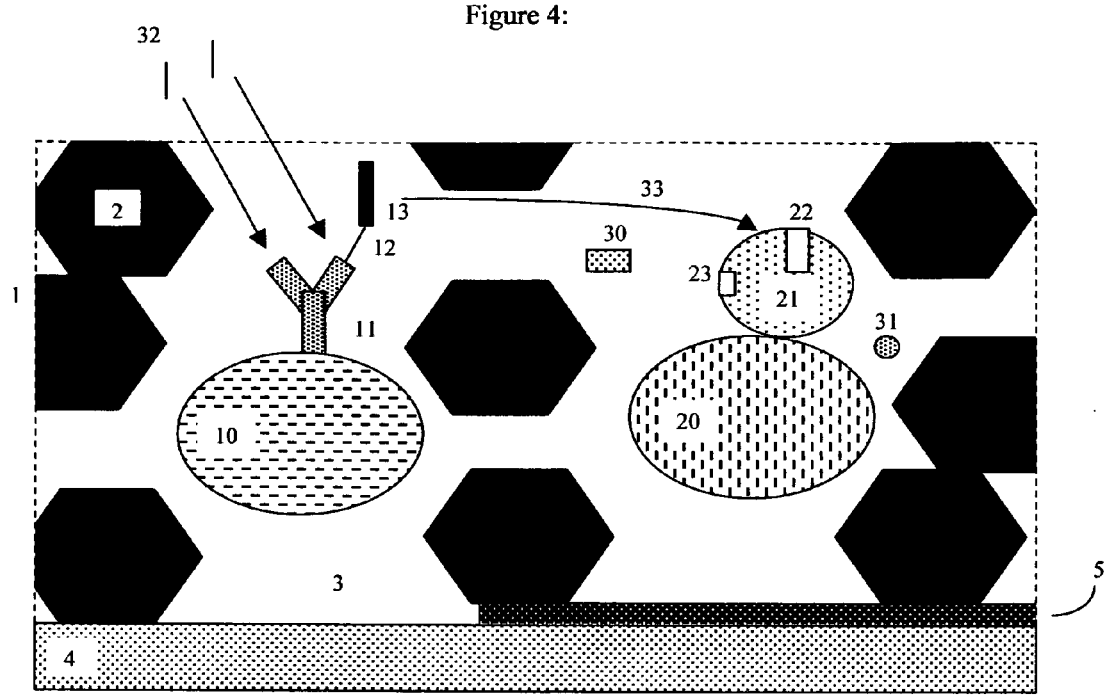
FIG. 4 shows an apoenzyme electrochemical immunoassay constructed using a porous electrode, microbead bound antibodies with bound ligand-prosthetic group conjugates, microbead bound apoenzymes, and a soluble electron transport mediator.
Figure 4:
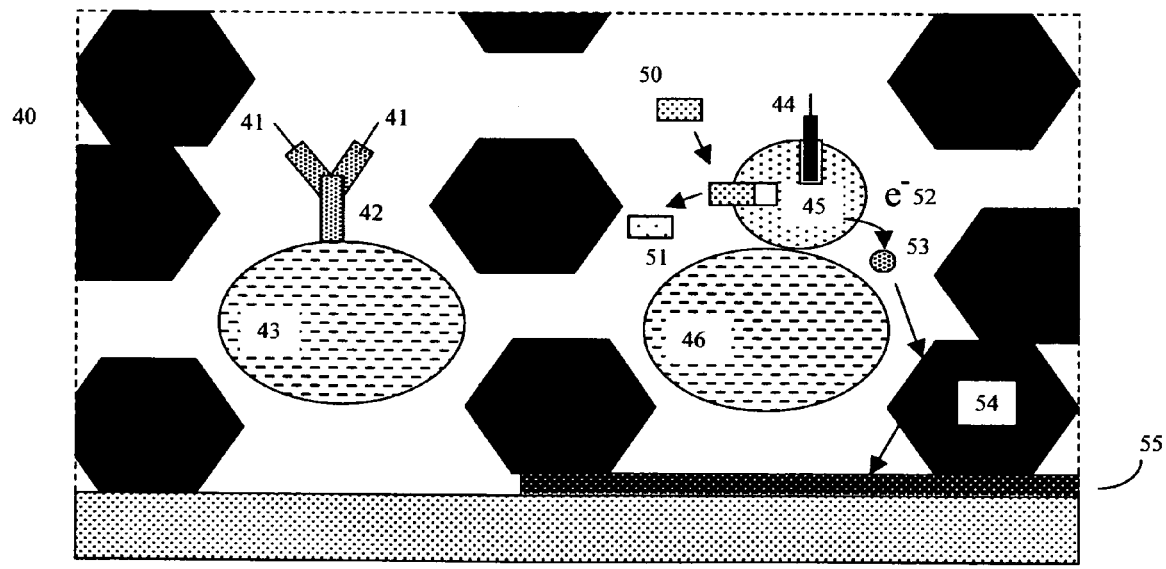

FIG. 4 shows an apoenzyme electrochemical immunoassay constructed using a porous electrode, microbead bound antibodies (which in turn bind ligand (antigen)-prosthetic group conjugates), microbead (microsphere) bound apoenzymes, and soluble electron transport mediators. This porous electrode (1) contains regions of electron transporting material (2), such as thin metal or carbon fibers, typically arranged in a open but connected three dimensional meshwork configuration that allows electrical transport over the length or width of the electrode, as well as multiple voids (3) of various sizes, at least some of which are in fluid communication with the outside surface of the electrode. Typically porous electrode (1) will be mounted on a carrier (4) that lends mechanical support and protection to the electrode. Electrical conducting traces (5) that allow electrical communication between the porous electrode (1) and outside electrochemical detection equipment are also typically present. Porous electrode (1) also contains a population of antibody-conjugated microspheres (10) and apoenzyme conjugated microspheres (microbeads) (20) within multiple voids (3). These microspheres (microbeads) are typically micron or sub micron sized particles with surface properties that enable proteins (such as antibodies and apoenzymes) to be tightly bound to the microbead surface. The porous electrode (1) typically has a pore size distribution large enough to enable a large percentage of the microbeads to penetrate a substantial distance into the interior of the electrode, but enough electrode structural material (2) as to at least partially hinder the microbeads from moving freely once the microbeads have penetrated into the interior of the electrode.

Antibody conjugated microsphere (10) contains bound antibodies (11). These antibodies are typically directed against the specific test ligands (antigens) that are the focus of interest for this particular immunoassay (e.g. anti-hCG antibodies for an hCG immunoassay, etc.) and contain binding sites for these test ligands (antigens). Prior to use, reagent complexes consisting of conjugates between the reagent ligand (antigen) (12) and the enzyme prosthetic group (13) are prepared, and are bound to the antibodies (11) bound to microbeads (10).

Apoenzyme conjugated microspheres (20) contain the apoenzyme itself (21) tightly coupled to microsphere (20). Typically, apoenzyme (21) will contain prosthetic binding site (22) and the enzyme active site (23) which, in the absence of the prosthetic group (13) will be in an inactive state.

The porous electrode (1) will typically also contain other reaction chemicals, such as the enzyme amplification substrate (30), electron transport mediator (31), apoenzyme stabilizing agents (such as trehalose), polymers (used to modulate the movement of microbeads within the porous electrode, as well as to modulate the flow of test fluids applied to the porous electrode surface), buffers, surfactants (used to encourage test fluid migration flow into the multiple voids (3)) and other ingredients as needed (not shown).

When fluid containing or suspected of containing test analyte antigens (32) is added to the surface of porous electrode (1), it permeates into the multiple voids (3) carrying test analyte (test antigens) (32). These test analytes (32) displace the binding between the antibody (11) and the reagent-antigen-enzyme prosthetic group conjugates (12), (13). The now liberated enzyme prosthetic groups (13) are now free to diffuse throughout the multiple voids (3) of porous electrode (1). Eventually, these liberated prosthetic groups (13) diffuse (33) to the prosthetic binding region (22) of apoenzyme (21), where they bind, causing apoenzyme (21) to now become a fully active enzyme.

The net effect of this test analyte induced enzyme reactivation is shown in the lower half of FIG. 4. Within the interior of porous electrode (40), ligands (41) from the test analyte have bound to antibody (42), which is still bound to antibody microbeads (43). The prosthetic group (44), has now bound to the prosthetic binding site and electrochemical apoenzyme (21) is now holoenzyme (enzyme) (45). Note that in this configuration, enzyme (45) remains attached to former apoenzyme microbead (20), now renamed enzyme microbead (46).

Reactivated enzyme (45) then converts its amplification substrate (50) to a reaction product (51). This reaction liberates electrons (52), which can flow, by way of electron transport mediator (53) to the electron transporting zones (54) of porous electrode (40). From here, the electrons may in turn pass into electrical conduits or traces (55), where an outside electrical measuring apparatus can then detect the reaction.

Figure 5:
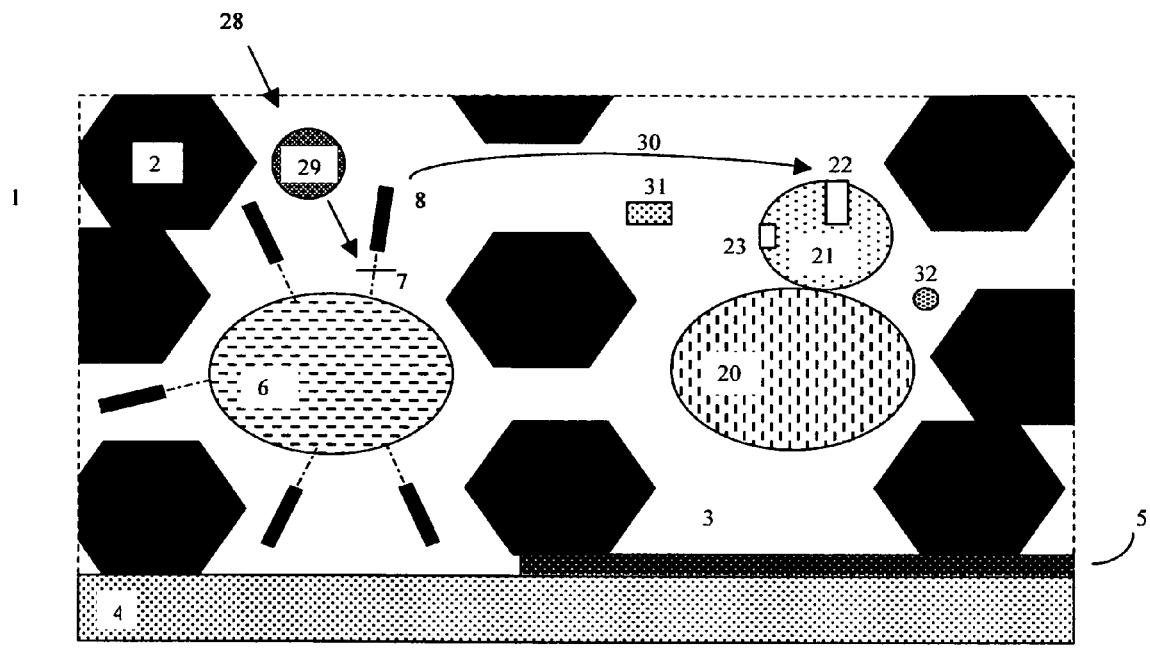
FIG. 5 shows an apoenzyme electrochemical protease assay (such as a coagulation assay) constructed using a porous electrode, microbead bound proteolytic enzyme (protease) peptide substrates capped with apoenzyme prosthetic groups, microbead bound apoenzymes, and a soluble electron transport mediator.
Figure 5:
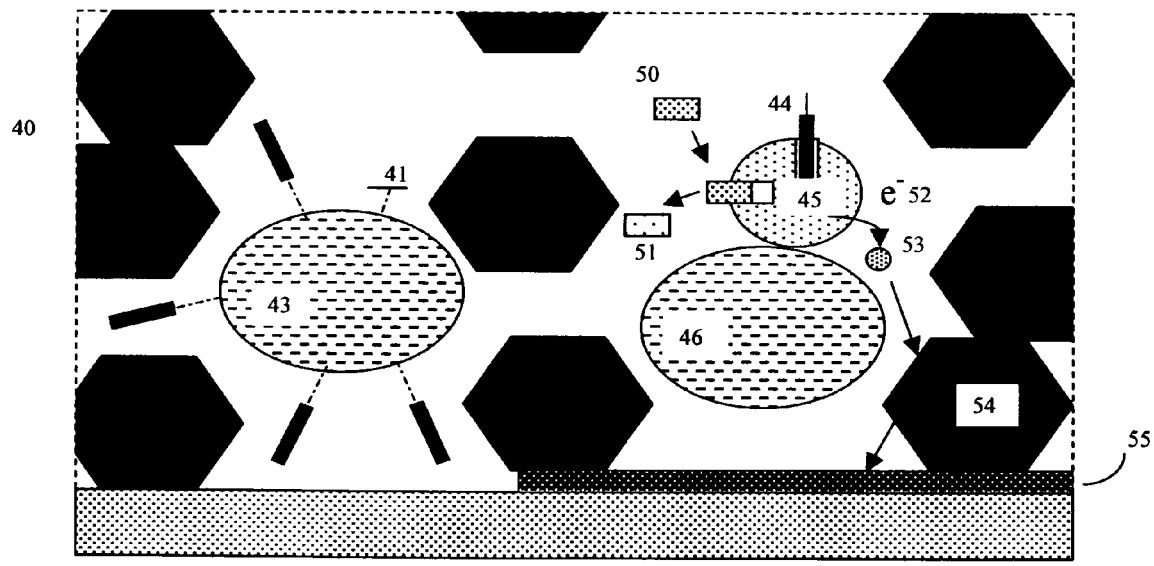

FIG. 5 shows that with some modifications, the microbead-porous electrode design previously shown in FIG. 4 can be configured for coagulation assays, protease assays, or other enzyme activity assays as well. FIG. 5 shows an apoenzyme electrochemical protease assay (such as a coagulation assay) constructed using a porous electrode, microbead bound protease test substrate peptides capped with apoenzyme prosthetic groups, microbead bound apoenzymes, and a soluble electron transport mediator.

This porous electrode (1) contains regions of electron transporting material (2), such as carbon or metal fibers, arranged in an open but connected three dimensional meshwork configuration that allows electrical transport over the length or width of the electrode, as well as multiple voids (3) of various sizes, at least some of which are in fluid communication with the outside surface of the electrode. Typically porous electrode (1) will be mounted on a carrier (4) that lends mechanical support and protection to the electrode. Electrical conducting traces (5) that allow electrical communication between the porous electrode (1) and outside electrochemical detection equipment are also typically present. Porous electrode (1) also contains a population of protease (proteolytic enzyme) peptide test substrate conjugated microspheres (microbeads) (6) and apoenzyme conjugated microspheres (20) within multiple voids (3). These microspheres are typically micron or sub micron sized particles with surface properties that enable proteins (such as peptides and apoenzymes) to be tightly bound to the microbead surface. The porous electrode typically has a pore size distribution large enough to enable a large percentage of the microbeads to penetrate a substantial distance into the interior of the electrode, but enough electrode structural material as to at least partially hinder the microbeads from moving freely once the microbeads have penetrated into the interior of the electrode.

Protease test substrate conjugated microsphere (6) contains peptides (7). These peptides, which are often formed by a solid phase peptide synthesis process using the microsphere (6) as the solid phase for the synthesis process, typically are covalently attached to the microsphere (6) by a peptide spacer group that is not itself a target for the assay protease enzyme, but rather serves to make the peptide test substrate region more sterically accessible to the assay protease analyte. These peptides (which may contain a spacer region, a protease substrate region, and optionally another spacer region are, in turned, capped by the assay's apoenzyme prosthetic group (8).

Apoenzyme conjugated microspheres (20) contain the apoenzyme itself (21) tightly coupled to microsphere (20). Typically, apoenzyme (21) will contain prosthetic binding site (22) and the enzyme active site (23) which, in the absence of the prosthetic group (8) will be in an inactive state.

The porous electrode (1) will typically also contain other reaction chemicals, such as the amplification substrate (31) for the electrochemically active enzyme, electron transport mediator (32), apoenzyme stabilizing agents (such as trehalose), polymers (used to modulate the movement of microbeads within the porous electrode, as well as to modulate the flow of test fluids applied to the porous electrode surface), buffers, surfactants (used to encourage test fluid flow into multiple voids (3) and appropriate protease initiators or coagulation pathway initiators, such as thromboplastin and calcium for a prothrombin time assay (not shown)).

When the test fluid (such as whole blood or plasma) containing coagulation test analytes (28) is added to the surface of porous electrode (1), it permeates into the multiple voids (3) carrying the various coagulation factors, exemplified by protease (29) in an active or inactive form. After coagulation factor (protease) (29) is converted to an active form (for coagulation assays, this is usually done by coagulation initiators that are included in the test strip's reaction chemistry), protease (29) cleaves its peptide test substrate (7), liberating the bound prosthetic group (8). The now liberated enzyme prosthetic groups (8) are now free to diffuse throughout the multiple voids (3) of porous electrode (1). Eventually, these liberated prosthetic groups (8) diffuse (30) to the prosthetic binding region (22) of electrochemical apoenzyme (21), where they bind, causing apoenzyme (21) to now become a fully active enzyme.

The net effect of this test analyte induced enzyme reactivation is shown in the lower half of FIG. 5. Within the interior of porous electrode (40), the cleaved protease test substrate peptide from the protease substrate (41) remains still bound to the peptide microbeads (43). The prosthetic group (44), has now bound to the prosthetic binding site and electrochemical apoenzyme (21) is now electrochemical enzyme (45). Note that in this configuration, enzyme (45) remains attached to former apoenzyme microbead (20), now renamed enzyme microbead (46).

Reactivated electrochemical enzyme (45) then converts its amplification substrate (50) to a reaction product (51). This reaction liberates electrons (52), which can flow, by way of electron transport mediator (53) to the electron transporting zones (54) of porous electrode (40). From here, the electrons may in turn pass into electrical conduits or traces (55), where an outside electrical measuring apparatus can then detect the reaction.

Typically, for both FIGS. 4 and 5, the electrochemical apoenzyme will be apoglucose oxidase, the prosthetic group is flavin-adenine dinucleotide (FAD), the amplification substrate is glucose and the product is gluconolactone.

FIGS. 4 and 5 both show configurations in which the apoenzyme is bound to a first bead population, and the antibody (or peptide test substrate) containing the ligand-bound prosthetic group is bound to a second bead population, both bead populations are embedded in a porous electrode, and both populations are interspersed with a diffusible electron transport mediator. Other configurations are also possible, however.

There are a number of ways in which these two bead populations can be embedded in a porous electrode, and the optimal way may vary according to the specifics of the assay. Although often the two bead populations may be simply be intermixed, for sensitive assays, the background signal caused by spontaneous apoenzyme reactivation brought about by occasional direct bead-bead contact may need to be reduced still further. This can be accomplished by adding additional "spacer" (separation) beads to the mix, by depositing the two bead populations in closely associated, but spatially distinct, regions on the electrode surface, or alternatively coated on different layers, one above the other.

Another alternative bead deposition pattern takes advantage of lateral flow techniques. This configuration is particularly favored for ultra sensitive immunoassays, where background signals due to stray interactions between the apoenzyme and the prosthetic group should be totally minimized. Here the immobilized antibody (either bound to microbeads or some other immobile test component), which in turn binds the ligand-prosthetic group, is placed upstream from the apoenzyme. When a liquid sample is applied, it flows (usually by capillary action) past a first region containing the immobilized antibody. If the antigenic test ligands are present, the test ligands displace the bound prosthetic group ligands from the antibody. These displaced prosthetic group ligands are carried, by the capillary transport of the liquid sample, into a second region containing the apoenzyme, electrode, an electron transport mediator, and an enzyme amplification substrate. Here, as before, the prosthetic group combines with the apoenzyme creating an electrochemically active enzyme, and the active enzyme converts the amplification substrate to the product. This produces electrons, which are carried by the electron transport mediator to the electrode.

One drawback of electrochemical electrodes based upon diffusible (soluble) electron transport mediators is low efficiency. The diffusible mediator shuttles back and forth between the enzyme and the electrode surface by a slow process involving diffusion and random walk style Brownian motion. By contrast, the work of Heller and others has shown that much higher efficiency can be obtained if the enzyme and electron transport mediator are both affixed to the electrode surface, and electrons can flow directly between the enzyme reaction center and the electrode by an electron transport mediator that is continuously attached to both the enzyme and the electrode surface. These techniques are frequently referred to as "wired enzyme" technology.

Figure 6:
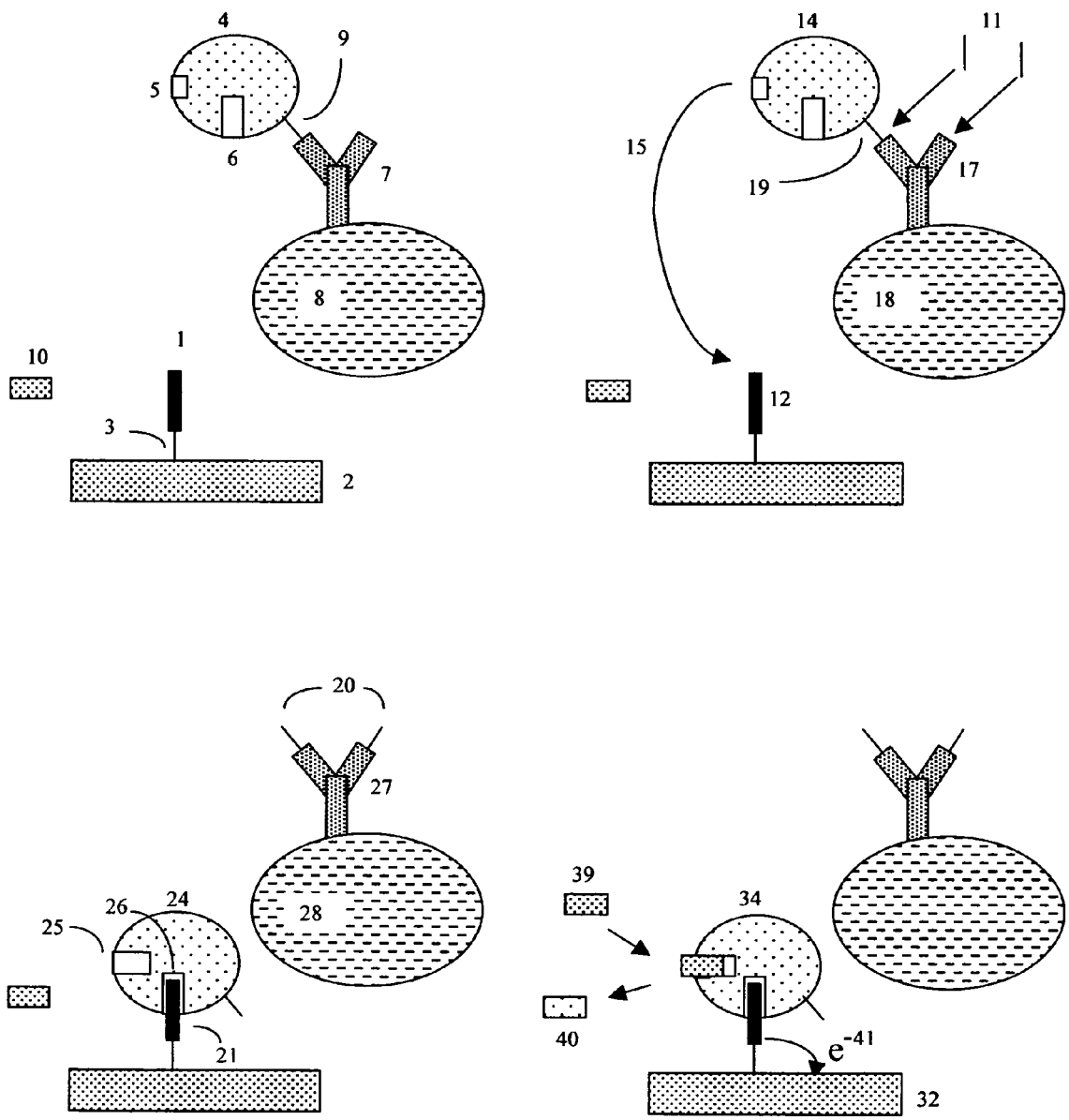
FIG. 6 shows an alternate form of the assay where the apoenzyme, liberated from a solid support, recombines with an enzyme prosthetic group that is bound to an electrode.

FIG. 6 shows an alternate apoenzyme immunoassay configuration which employs some of the "wired enzyme" concepts of Heller et. al., and physical separation between the apoenzyme and the prosthetic group, to improve assay efficiency. In this configuration, a non-enzyme complexed prosthetic group, such as FAD (1) is bound to an electrode surface (2) by bridging means (3) that act to facilitate electron transport. An apoenzyme (4) containing an active site (5) and a prosthetic group binding site (6), and an artificially coupled reagent-ligand group (antigenic group) (9), is bound to an antibody (7). This in turn is bound to a distant surface (8), such as a microbead or different location on the enzyme electrode. Enzyme amplification substrate (10) is also present.

When antigenic test ligands (11) are added to the system, they compete for binding between the antigenic reagent ligand group (19) previously coupled to the apoenzyme (14), breaking the bond between the antigenic reagent ligand group (19) and the antibody (17). This allows apoenzyme (14) to diffuse away (15) from sterically isolated bead or surface (18), and towards electrode bound prosthetic group (12).

The prosthetic group binding region (26) of apoenzyme (24) then binds to the electrode bound prosthetic group (21). Apoenzyme (24) is reconstituted to an active enzyme (24) configuration, and the active site (25) of enzyme (24) changes from an inactive configuration to an active configuration. Note that the ligand binding sites on nearby antibody (27) bound to physically isolated bead or surface (28) remains complexed with test ligand (20).

After enzyme activation is complete, now reconstituted electrochemical enzyme (34) converts the enzyme amplification substrate (39) to its reaction product (40), generating electrons (41) that transfer to the electrode surface (32). This electron transfer occurs through a direct link between the enzyme prosthetic group and the enzyme surface.

Figure 7:
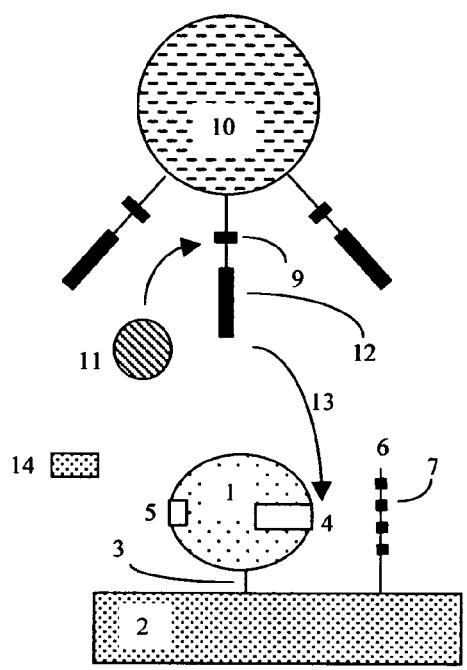
FIG. 7 shows two other formats of the assay; a first format in which the apoenzyme is anchored to an electrode surface that also contains a hydrogel with embedded electron transport groups, and a second format in which the apoenzyme is bound to an electrode surface, and is reactivated by a molecule containing a conjugate of the prosthetic group and an electron transport mediator.
Figure 7:
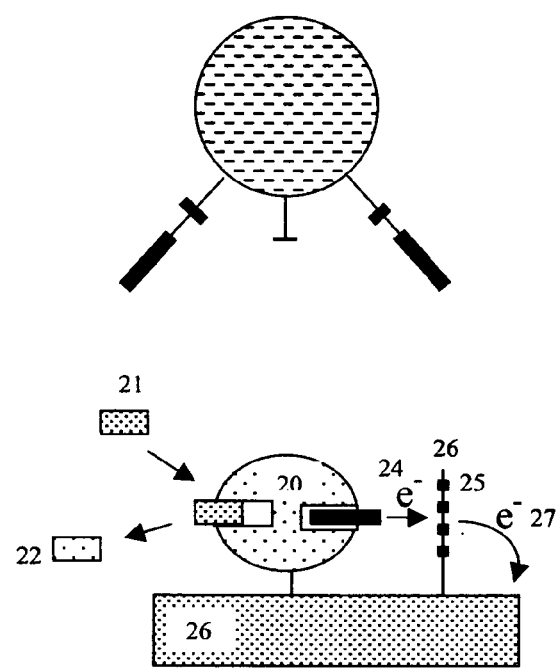
Figure 7:
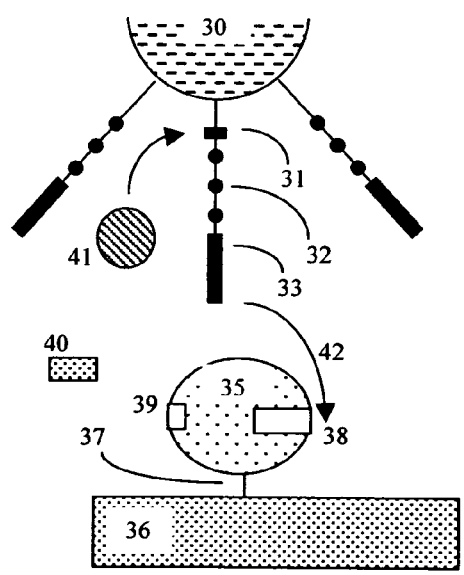
Figure 7:
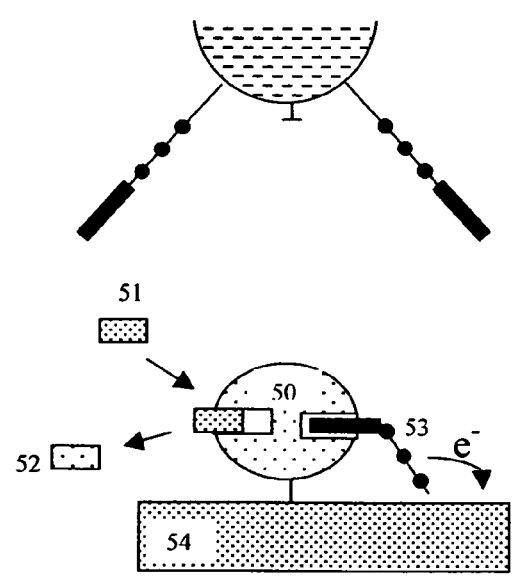

Other "wired enzyme" configurations, in which a group other than the prosthetic group binds the apoenzyme very close to the electrode, are also possible. Two of these configurations are shown in FIG. 7. In the top part of FIG. 7, the apoenzyme (1) is bound to an electrode surface (2) or a surface associated hydrogel by a non-prosthetic group link (3). As before, apoenzyme (1) contains prosthetic group binding region (4) and an active site region (5). Typically, enzyme (1) will be closely associated with hydrogel (6) containing electron transport mediator groups (7).

As before, the proteolytic peptide enzyme substrate (9) is anchored on microbeads (10) or other support that enables the enzyme substrate to be physically separated from the apoenzyme (1) until the peptide protease substrate (9) is cleaved by the appropriate protease (11). As before, the protease peptide enzyme substrate (9) is capped with apoenzyme prosthetic group (12).

When proteolytic enzyme (protease) (11) cleaves the test substrate peptide (9), the prosthetic group (12) is liberated and can diffuse (13) to and bind with the prosthetic group binding region (4) of electrochemical apoenzyme (1). Typically amplification enzyme substrate (14), as well as other reaction chemicals (coagulation initiators, buffers, viscosity modifying polymers, and apoenzyme stabilizing agents such as trehalose) are also present.

After the prosthetic group has recombined with the apoenzyme, forming electrochemically active enzyme (20), the active enzyme converts its amplification substrate (21) to the reaction product (22) producing an electrochemical change. Electrons from this electrochemical change (24) are transferred to electron transport mediators (25) bound to the hydrogel attached to the electrode (26). These electron transport mediators (25) in turn transfer (27) electrons to the electrode (26).

In an alternate configuration, the proteolytic enzyme peptide test substrate itself contains an electron transport mediator as well as an apoenzyme prosthetic group. This configuration is seen in the lower half of FIG. 7.

In this configuration, the enzyme prosthetic group may be coupled to one or more electron transport mediators by a tether, and this tether in turn coupled to the protease substrate peptide, and this peptide in turn attached to an anchor group. After the protease test substrate peptide is cleaved by the coagulation protease, and the liberated prosthetic group—electron transport mediator conjugate diffuses over to reactivate the apoenzyme, these tethered electron transport mediators can then extend the distance to which electrons can easily be transported away from the now reconstituted apoenzyme (enzyme). If this electrochemically active enzyme in turn is bound to an electrode surface, then if the tethered electron transport mediators are sufficiently long, they can transport electrons between the electrochemically active enzyme's reaction centers and the electrode surface with an efficiency that is relatively high.

As shown in the lower half of FIG. 7, peptide protease test substrate groups (31) are again built up around micron sized plastic microspheres (30) with free carboxyl terminal ends using standard solid phase peptide synthesis techniques, such as Fmoc solid phase peptide synthesis (Chan and White editors, "Fmoc Solid Phase Peptide Synthesis, A practical approach", Oxford University Press, 2000). After the desired spacer and protease test substrate site are built up, the peptide chains are then coupled to an electron transport mediator (32), such as Pyrroloquinoline quinine (PQQ). They are in turn coupled with an electrically active enzyme prosthetic group (33), such as $N^6$-(2-aminoethyl)-FAD, resulting in microspheres coupled with chains of protease test substrate, electron transport mediators, and enzyme prosthetic groups all arranged in a linear order.

In this configuration, the apoenzyme, such as apoglucose oxidase (35) is bound to an electrode surface (36), by non-prosthetic group linkage (37). This linkage may be a covalent linkage such as a covalent crosslink, a hydrophobic linkage, an electrostatic linkage, an antibody linkage or so on. This apoenzyme will typically have a prosthetic group binding region (38) and an enzyme active site (39), which, in the apo state, will typically have an inactive conformation. The test will also contain excess amplification substrate (40) for the electrochemically active enzyme, as well as other chemicals and cofactors needed to stimulate the desired coagulation protease reaction (such as thromboplastin and calcium for a prothrombin time test, etc.) (not shown).

After the relevant protease has been generated (41) (thrombin in the case of a prothrombin time test), detection proceeds as follows. Protease (41) cleaves its corresponding synthetic peptide test substrate (31), liberating the chain that contains the enzyme prosthetic group (33) and tethered electron transport mediator (32) away from the support (30).

This liberated chain is then free to diffuse (42) and bind to the prosthetic group binding site (38) of nearby electrode bound enzyme (35). There the prosthetic group—tethered electron transport mediator (32, 33) reactivates the electrochemically active enzyme.

The reactivated electrochemical enzyme (50) starts converting its amplification substrate (51) to product (52). Electrons flow through the prosthetic group and through the tethered electron transport mediator (53) to electrode surface (54).

It should be apparent that the general schemes shown in FIGS. 6 and 7 apply to both immunochemical assays, coagulation (protease) assays, and substrate cleaving hydrolase enzymatic assays, and that with minor modification, the scheme of FIG. 6 will work for protease and hydrolase assays. Likewise, with minor modification, the schemes of FIG. 7 will work for immunoassays.

Figure 8:
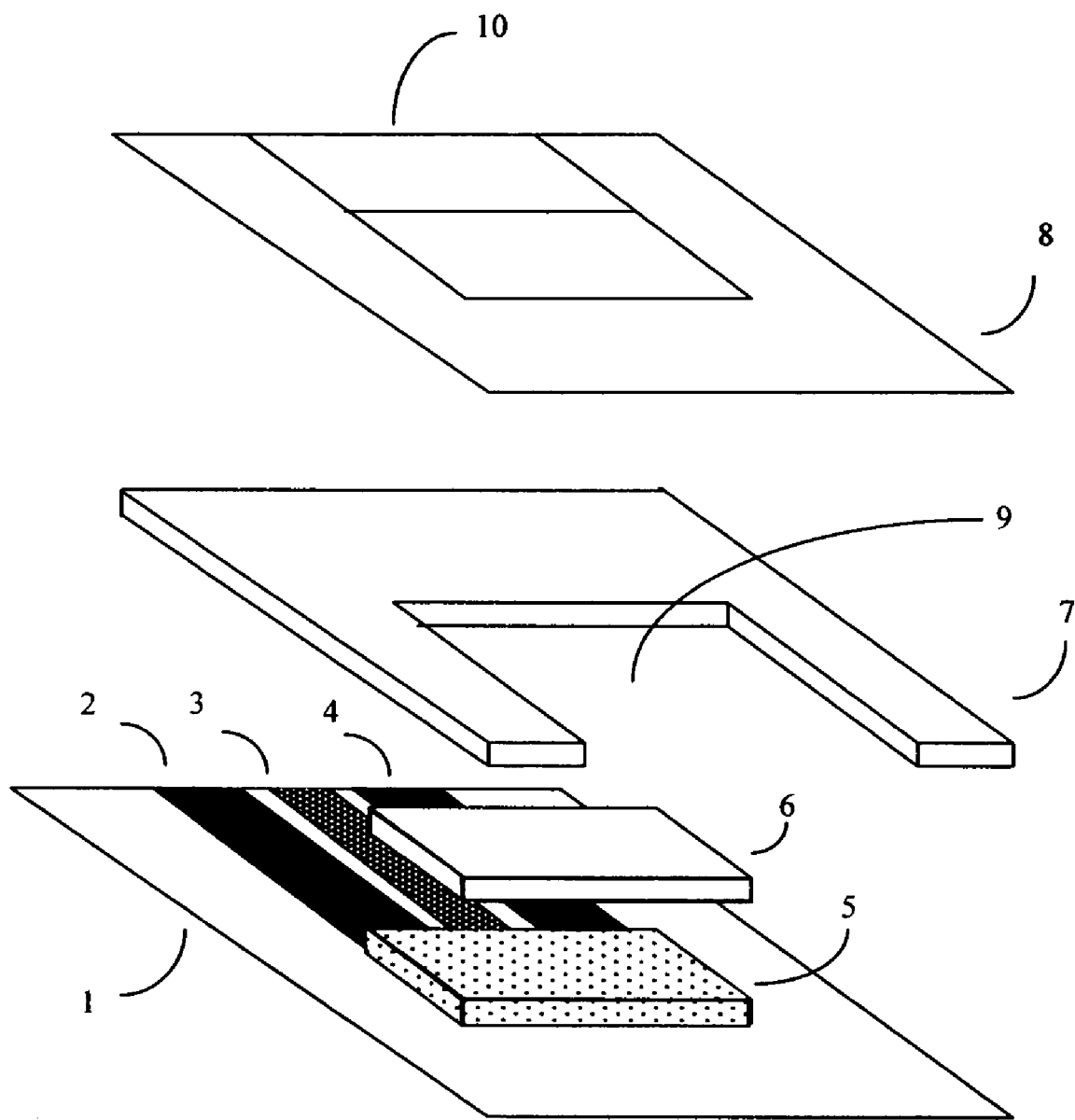
FIG. 8 shows a drawing of an apoenzyme electrochemical detection test strip.

FIG. 8 shows a diagram of one possible apoenzyme electrochemical test strip. Here the test strip has a bottom plastic support (1), a first conducting electrode (2), an optional reference electrode (3) and a second conducting electrode (4). The porous electrode configuration containing the apoglucose oxidase, electron transport mediator, test analyte detection moiety conjugate, and the amplification substrate glucose (previously shown in FIGS. 4 and 5) is shown as (5). This porous electrode is put into electrical contact with electrodes (2, 3, 4) by a conducting adhesive.

In the case where the assay is a coagulation assay, such as a prothrombin time test, the test strip may additionally contain a dry thromboplastin pellet (6). For other coagulation tests, a different coagulation initiator may be used. For immunochemical tests, pellet (6) may be omitted. For coagulation assays, if the porous electrode is sufficiently coagulation neutral (as defined in U.S. Pat. No. 5,580,744, the contents of which are incorporated herein by reference), then the thromboplastin (or other coagulation initiator) in pellet (6) may be physically located inside porous electrode (5). In an alternative configuration, which is particularly useful if the porous electrode is not sufficiently coagulation neutral, the thromboplastin pellet (6) may be located outside of porous electrode (5). In this later configuration, the test strip configuration may be optimized so as to allow the liquid sample to hydrate the thromboplastin (or other coagulation initiator) pellet (6) first, and then contact the porous electrode (5) after a slight time delay (preferably on the order of a second or less) that allows the coagulation process to begin.

Plastic spacer (7) is present to separate the plastic sheet (1) containing electrodes (2, 3, 4) from the top plastic covering (8). Plastic spacer (7) has a "U" shaped opening that creates a cavity (9). Cavity (9) is used both to hold the pellet (6), as well as to receive the blood sample from the patient. In practice, cavity (9) has a configuration such that it can be totally filled with about 1-50 microliters of sample.

In some configurations, plastic layer (8) also holds a reference electrode (10). In the operating configuration, layers (1), (7) and (8) are laminated together to form a single unitized structure electrically connected to the outside by conductive paths (2, 3, 4 and 10), and in liquid communication with the outside through cavity (9).

For temperature sensitive tests, such as coagulation assays, it is often advantageous to employ means to keep the test strip at a constant temperature, such as 37° C., throughout the reaction. This may be done by various heat transport mechanisms. One simple means is to put the test strip into a cavity formed from a heat conductor made of a material with good heat exchange properties (such as copper), and employ electronic means to keep the heat sink at a constant temperature. Here, the tip of the "U" shaped sample receiving end of the test strip (6) sticks out slightly from the cavity to facilitate sample application, but the electrode base of the strip, as well as the back of the "U" shaped cavity remain inside the heat sink cavity, and thus are warmed to a constant temperature.

For high volume commercial applications, it may be desirable to produce an extremely low cost reagent reader (meter) with minimal onboard temperature regulation means. In such cases, where a somewhat higher cost electrochemical reagent test strip is acceptable, it may be advantageous to embed a temperature sensor and/or electrical heater directly into the reagent test strip itself. This can be done, for example, by embedding a low-cost thermistor and/or electrical resistance heater into or onto the plastic support (for example elements (1) or (8) in FIG. 8) that also holds the other test strip components. In this later configuration, the reagent test strip reader (meter) need only contain electrical means to read the thermistor and electrical means to apply electrical energy to the heater onboard the test strip itself, and thus the meter will have a simplified and lower cost configuration.

Onboard controls: In some situations, it may be advantageous to include multiple electrodes in a single test strip in order to obtain both positive (high) and negative (low) onboard controls for the reaction. For a coagulation test, the positive (high) control can be obtained by using a control electrode with an alternate peptide substrate that is not sensitive to the particular protease used in the reaction. Similarly a negative (low) control can be obtained by using free FAD (or appropriate prosthetic group). Other control chemistry is also possible.

For an immunochemical test, positive control (high) control can be obtained by using a control electrode with free FAD (or appropriate prosthetic group), and a negative (low) control can be obtained by using FAD linked to a different antibody using a different ligand. Other control chemistry is also possible.

Other Applications:

Other immunochemical applications for this technology include tests for sepsis, angiogenesis, pregnancy and ovulation, cardiovascular status, infectious disease, drugs of abuse, therapeutic drugs, kidney disease, ischemia, and cancer diagnostics. Sepsis markers include calcitonin, procalcitonin, C-reactive protein, endogenous activated protein C, tumor necrosis factor, interleukin-6 and 10, endotoxin, lipopolysacharide binding protein, and pro-atrial natriuretic peptide. Angiogenesis markers include the markers discussed in copending application Ser. No. 10/233,908. Infectious disease markers include C difficile, Hepatitis, HIV, influenza, legionelly, pneumonia, RSV, strep, and syphillis. Pregnancy and ovulation markers include early pregnancy factor, human chorionic gonadotropin and luteinising hormone (LH). Drugs of abuse include amphetamines, barbiturates, benzodiazepines, cocaine, methamphetamines, opiates, phencyclidine, THC, and trycyclic antidepressants. Therapeutic drugs (in particular narrow therapeutic index drugs) include small molecule therapeutic drugs, acetaminophen, carbamazepine, phenyloin, and theophylline, and larger molecule drugs such as drotrecogin alfa (Xigris®), tissue plasminogen activator, and others. Kidney disease and injury markers include cystantin C, neutrophil gelatinase-Associated lipocalin, interleukin-18, kidney injury molecule-1 (KIM-1), and proatrial-natriuretic peptide (1-98). Ischemia and cardiovascular injury markers include d-dimer, troponin I, creatine kinase-MB, myoglobin, nt Pro BNP, ischemia modified albumin, S-100 beta and myeloperoxidase. Various cancer diagnosis markers include prostate specific antigen, and other markers described in copending application Ser. No. 10/233,908.

In addition to various immunochemical tests, the disclosures of the present application are highly relevant to various enzymatic tests. As discussed in copending U.S. application Ser. No. 10/233,908, incorporated herein by reference, there are a number of important disease states where rapid "point-of-care" type access to complex enzymatic activity patterns, in particular complex protease systems, is clinically useful. These situations include tumor vascularization, angiogenesis, arthritis, vascular proliferative disorders, coagulation disorders, sepsis, and microbial assays.

For both immunochemical and enzymatic applications, in many cases a single diagnostic marker does not give a full picture. Rather, multiple biomarkers often give superior clinical information, and this information can be used to help produce superior clinical outcomes for the disease state in question. For these applications, it will often be useful to construct microarrays (or other form of diagnostic sensor) composed of multiple electrochemical enzyme or antigen detectors, each communicating with the outside world through an electrode network that allows the electrical signal from a particular detection element to be analyzed by outside instrumentation. Such a multiple element sensor, ideally activated by single drop of fluid from a clinical sample, would allow the status of the sample in question to be almost instantly assessed. This would allow healthcare personnel to almost instantly assess the clinical status of a patient (e.g. risk of sepsis or septic shock, angiogenic potential of a tumor while the patient is still on an operating table, etc.), and take immediate action as appropriate.

EXPERIMENTAL

Preparation of Apoglucose Oxidase Conjugated Microbeads, Antibody Conjugated Microbeads, and Protease Substrate Conjugated Microbeads Apoglucose oxidase conjugated microbeads: Apoglucose oxidase can be prepared by a number of methods. One of the more modern, and particularly favored, methods is according to the methods of Heiss et. al. (Dip-and-read test strips for the determination of trinitrotoluene (TNT) in drinking water; Carola Heiss, Michael G. Weller, Reinhard Niessner: Analytica Chimica Acta 396 (1999) 309-316). Briefly, The FAD groups from Glucose oxidase (*Aspergillus niger*, Sigma-Aldrich Corporation) can removed by dissolving the Glucose oxidase in a CHAPS, 30% glycerol, HCL/glycine buffer at pH 1.5. The apoglucose oxidase can then be separated from the unbound FAD groups by gel chromatography in Toyopearl HW-50 F columns in 30% glycerol, 70% HCL/glycine buffer at pH 1.5. Residual FAD groups can be removed by suspending the column eluate directly into a 38 mg/ml suspension of stirred charcoal, and then readjusting the pH to 7.0 to avoid protein denaturation. Residual charcoal is removed by centrifugation, and the supernatant filtered through a 0.2 um polysulfone filter to remove remaining aggregates.

The apoglucose oxidase solution should then be immediately desalted by running the supernatant through a Chemcon spin-OUT™-6000 micro chromatography column equilibrated in 0.1 M sodium phosphate buffer, pH 7.0. The eluate from this column should then be immediately coupled to 1.0 micron diameter carboxyl modified latex microbeads (Bangs Labs) by carbodiimide coupling, following the materials and procedures contained in Polysciences PolyLink Protein Coupling Kit #644. After coupling, reaction quenching, and washing according to the Polysciences protocol, the apoglucose coupled latex microbeads are spun down in a microfuge, and resuspended in a 1.5M trehalose, 5 mg/ml BSA, PBS buffer for storage. Ideally apoglucose oxidase preparation and the bead coupling reaction should be done on the same day to reduce the level of formation of unwanted apoglucose oxidase aggregates.

Antibody conjugated microbeads: Monoclonal antibodies against the target analyte of interest can usually be obtained from many different commercial sources. These are typically then put into 0.1 M phosphate buffer, pH 7.0 by dialysis or microcolumn separation and suspended at a concentration of about 1 mg protein per ml of buffer. These can then be conjugated onto 1.0 micron COOH latex microspheres (Bangs Labs) by carbodiimide coupling between the carboxyl groups on the surface of the microbead and the primary amines on the protein of interest using the same PolyLink—Protein Coupling Kit for COOH Microparticles (PolySciences, Inc., Warrington Pa.) discussed previously.

Protease test substrate conjugated microbeads: The protease test substrate peptide of interest (typically a thrombin substrate peptide) is built up on small (micron diameter) resin microbeads using standard Fmoc solid phase peptide synthesis techniques. (Fmoc Solid Phase Peptide Synthesis, A practical approach, W. Chan and P. White editors, Oxford University Press, New York, 2000). After the desired test substrate peptide, which usually will contain a spacer region both before and after the actual substrate region itself to facilitate steric access to enable the protease of interest to later cleave the desired peptide, is constructed, the N terminal blocking group is removed, and a FAD (or other apoenzyme prosthetic group) is placed on the N terminal end of the microbead bound protease substrate peptide using the FAD-peptide conjugation methods discussed below.

FAD-Peptide Conjugation Methods:

N6-aminohexyl-flavin adenine dinucleotide can be synthesized according to the methods of Morris et. al. (Morris D L, Ellis P B, Carrico R J, et al. Flavin adenine dinucleotide as a label in homogeneous colorimetric immunoassays. Anal Chem 53, 658-665 (1981)).

FAD can be coupled to peptides and proteins by the methods of Schroeder et. al. (Schroeder H R, Dean C L, Johnson P K, Morris D L, Hurtle R L.; Coupling aminohexyl-FAD to proteins with dimethyladipimidate. Clin. Chem. 1985 September; 31(9):1432-7; and Morris D L, Buckler R T. Colorimetric immunoassays using flavin adenine dinucleotide as label. Methods Enzymol. 1983; 92: 413-25.). Briefly N6-aminohexyl-flavin adenine dinucleotide is activated with dimethyladipimidate, run through a Sephadex G-10 gel filtration column in 20 mM $NaHCO_3$ buffer to remove unbound imidate, and then incubated with the target protein. If the target protein in question is a protease test substrate peptide bound to a microbead, after conjugation, the now FAD conjugated protease test substrate peptide—microbead complex can then be washed by repeated centrifugation and resuspension. If the target molecule in question is a soluble protein antigen (such as the analyte for an immunoassay) the conjugated target proteins (reagent antigens) can be purified by a second gel separation column in Sephadex G-25 in 100 mM phosphate buffer, pH 7.0 (which separates the unbound FAD-imidate from the FAD conjugated protein).

Porous Electrode Methods:

Porous carbon electrodes (Torayca Carbon paper TGP-H-120) can be obtained from Toray Industries Corporation, Japan, through a US distributor (FuelCellStore.com, Boulder Colo.). This material is a loose meshwork of connected electrically conducting carbon fibers, and has a structure similar to loose weave filter paper, with large (approximately 50 micron) holes and voids in-between the various thin and interconnected carbon filaments. This material is produced in various thicknesses. One exemplary grade (TGP-H-120) is 0.37 mm thick, has an in-plane electrical resistance of about 4.7 mega ohms per centimeter, is 78% porous, and has a bulk density of 0.45 grams per cubic centimeter. It is highly permeable, and allows passage of gas at a level of (1500 ml gas*mm)/($cm^2$*hour*mmAq). Thinner grades of this material are also available, and may be appropriate when use of lower volumes of analyte sample is desired. The carbon paper is hydrophobic, and can be rendered hydrophilic by various methods including plasma oxidation, or by pretreatment with appropriate surfactants such as an aqueous solution of 0.1 mg/ml tyloxapol (which is a gentle surfactant that, in low concentrations, does not lyse red cell membranes).

Note that other workers have found that the efficiency of carbon paper electrodes can be improved by additionally growing carbon nanotubes on the carbon paper base, or by adding additional conducting microparticles to the carbon paper base. Such methods are highly compatible with the apoglucose oxidase reconstitution methods described in this disclosure, as the nanotubes or conducting particles increase the available electrode surface area, and thus increase electron transfer efficiency.

Electron transport mediator: Although, depending upon the particular configuration, almost any type of electron transport mediator may be used for the present invention, methylene blue has certain advantages for the porous carbon paper—microbead electrode configurations described here. Methylene blue (Calbiochem Corporation, San Diego, Calif.) is an electron transport mediator with good solubility in water, and thus is available in relatively high concentrations in order to shuttle electrons over the comparatively large (up to several microns) distance between the microbead bound glucose oxidase, and the carbon electrode surface of the porous Toray carbon paper electrode. Methylene blue is also inexpensive, known to be compatible with glucose biosensors, relatively non-toxic, and readily available.

Test Strip Production Methods:

For immunoassays, the antibody conjugated microspheres can be bound to the FAD (or other prosthetic group) conjugated reagent antigen complex by incubating the microspheres with the FAD conjugated reagent antigen for 30 minutes, followed by washing 3× by centrifugation and resuspension before use to in order to remove unbound FAD-reagent antigen conjugates.

All microspheres should be reconstituted (separately) in a solution of about 1% microspheres, 50 mM phosphate buffer pH 7.0, 0.1 M NaCl, 1.5 M trehalose (to stabilize the apoglucose oxidase), 5 mg/ml protease free bovine serum albumin, 10 mg/ml Polyvinyl alcohol, 0.1 mg/ml Methylene blue, 0.1 mg/ml tyloxapol (to help disperse the microspheres, and also help improve solubility), 50 mM Glucose (enzyme substrate for the reconstituted glucose oxidase).

To reduce the amount of microsphere aggregation, microsphere solutions should be sonicated briefly, and then immediately applied to the porous carbon paper using a low volume micro airbrush, such as an Iwata HP-A airbrush. Depending upon the specifics of the experiment, various deposition patterns can be used. In one configuration, a first coating of apoglucose oxidase microspheres is applied, the carbon paper dried using a hot air dryer, and then a second coating of antibody microspheres containing the bound FAD-reagent antigen groups is then applied, immediately followed by drying using a hot air dryer. In other configurations, the separation between the apoglucose oxidase microspheres and the antibody microspheres can be increased by coating one side of the carbon paper with the apoglucose oxidase microspheres, air drying, and then coating the other side of the carbon paper with the antibody microspheres, followed by rapid air drying. In a third configuration, unconjugated spacer microspheres may be used. Here the apoglucose oxidase microspheres are applied and air-dried. The spacer microspheres are then lightly applied, and air-dried. Finally the antibody conjugated microspheres (or peptide substrate microspheres are then applied).

For immunoassays, no further test chemistry is required. For coagulation assays, such as prothrombin time tests, coagulation initiators such as thromboplastin and calcium are required. If suitable coagulation neutral microbeads and electron transport mediators are provided per the methods of Zweig, (U.S. Pat. No. 5,580,744), then the thromboplastin and calcium can be applied to the porous carbon matrix itself, and all steps of the reaction proceed inside the electrode matrix.

In some cases, such as when the porous electrode, thrombin substrate, apoenzyme, and electron transport mediators are not entirely coagulation neutral, it may be advantageous to begin at least the initial phases of the coagulation reaction immediately outside the porous electrode, and allow the coagulation proteases, such as thrombin, to diffuse into the porous electrode, where they may then be detected. In this later situation, the porous electrode will often be mounted on one side of the test strip chamber, thromboplastin and calcium placed in a different part of the test strip, and small amounts of whole blood allowed to flow into the test strip chamber by capillary action. The blood or plasma first contacts the thromboplastin, starts the coagulation process, and produces soluble coagulation factors, which then migrate into the electrode where the reaction can be detected.

After impregnation with the appropriate reaction chemistry, the carbon paper electrodes can then be affixed to larger and more mechanically robust electrically conducting surfaces, usually on plastic supports, suitable for relaying the signal to appropriate instrumentation. These conductors are typically vitreous carbon electrodes, carbon paste coated plastic, and silver-silver chloride electrode coated plastic supports. Binding to the porous electrode can be done using various conducting adhesives, such as the conducting adhesives used to adhere materials to electrodes for scanning electron microscopy purposes, which are provide by Structure Probe, Inc (SPI), West Chester, Pa. This includes, SPI Conductive Carbon Paint; SPI LEIT-C™ Conductive Carbon Cement and Thinner; and SPI Supplies® Brand Conductive Double Sided Carbon Adhesive Tape.

Other electrically conducting traces and electrode components are available from other vendors. For example, silver-carbon screen-printing paste C70709D14, and reference electrode silver-silver chloride polymer paste C61003D7 may be obtained from Gwent Electronic Materials Ltd., Pontypool, UK. This reference silver/silver-chloride paste is a mixture of fine (roughly 10 micron sized) silver and silver-chloride particles present in a roughly 60% silver, 40% silver chloride ratio. These particles are held in a polymeric binder support. The electrode formed from this material acts as a standard silver chloride reference electrode for the reaction.

The various plastic support layers, containing the transfer electrodes, can then be laminated together with an additional 10 mil (0.254 mm) to 30 mil thick spacer layer to result in a sandwich electrode with 10 mm×10 mm sized electrode surface area, and an internal volume of about 10 ul to 30 ul. This is shown in FIG. 8. Note that the electrodes on surfaces (8) and (1) all face the interior of the cavity.

Both two electrode and three electrode (using a Ag—Ag—Cl reference electrode) designs are possible with this configuration. In general, three electrode designs incorporating a reference electrode, although more expensive and difficult to produce, are preferred due to their higher sensitivity and accuracy.

Electrochemical Sensing Methods

The electrochemical activity of the electrodes can be assessed with a series of linearly variant patterns of potential versus time sweeps (Cunningham, "Introduction to Biolanalytical Sensors", Wiley Interscience, 1998 p 207-259). One low cost device that functions well, with an optional external amplifier to bring up weak signals, is an IBM EC/225 Voltammetric Analyzer (IBM corporation). Because the reconstituted apoenzyme electrodes generate a comparatively weak signal (relative to standard glucose electrodes), more sensitive potentiostats, such as a Bioanalytical Systems LC-4B amperometric detector, with sensitivity to current that extends down into the picoamp range, can also be used. The offset voltages that are used typically vary according to the choice of electron transport mediator, but typically are about 0.5 V for methylene blue. The output from these devices can then be either manually recorded, or stored in a computer file as desired.

Experiment 1

Immunochemistry experiment using antibody conjugated beads and a porous electrode. This experiment exemplifies the use of indirect "sandwich" immunoassays by constructing an apoenzyme electrochemical immunoassay sensitive to rabbit IgG. To do this, 1-micron COOH microbeads should be conjugated with a first monoclonal antibody directed against rabbit IgG, using previously described methods. A second mouse monoclonal antibody, directed against a different epitope on rabbit IgG, should be conjugated with FAD, again using previously described methods.

The desired detection complex is somewhat like a sandwich with the bead-capture antibody (here the bead antibody is a first anti-rabbit IgG antibody) forming the first layer, the antigen (here rabbit IgG is used as the antigen) forming the middle layer, and the FAD-conjugated anti-antigen antibody (here a second anti-rabbit IgG antibody that binds to a different epitope on rabbit IgG) forming the top layer. This structure is built up in stages, and the beads are washed in-between each stage. First the middle layer is added to the first layer, and then the top layer is added to the middle layer and lower layer.

Purified rabbit IgG should be suspended 0.1 M Phosphate buffered saline, pH 7.0, at a concentration of 0.1 mg/ml, and incubated with a 1% solution of the mouse-anti-rabbit IgG conjugated microbeads for 1 hour, washed 3× in the same buffer by repeated microcentrifugation, and then resuspended to the original 1% concentration.

To add the top layer to the sandwich, the FAD-conjugated monoclonal mouse anti rabbit IgG should then be added to these washed microbeads to a final concentration of 0.2 mg/ml of antibody, and allowed to bind for 1 hour. The beads should be washed 3× in phosphate buffer, and resuspended in the 1.5M Trehalose buffer at a 1% suspension.

The net result is to create a sandwich structure of the type:

[Bead]-(Anti-rabbit IgG) (rabbit IgG) (Anti-rabbit IgG)-FAD in which the FAD-conjugated anti-rabbit IgG monoclonal antibody binds to the rabbit IgG, which in turn binds to the anti-rabbit IgG coupled to the beads.

These beads should be deposited using an airbrush on porous Toray carbon paper electrodes, along with the apoglucose oxidase microbeads, as described previously. This electrode then should be mounted on a solid support containing leader electrodes using the conductive adhesives described previously.

A plastic cover should be laminated on top of the porous carbon electrode—support layer with a 10-30 mil thick plastic spacer, creating a lower support, porous carbon electrode, upper plastic support structure as shown in FIG. 8.

The test strip is attached to the electrochemistry measuring apparatus. When challenged with 0.1 M Phosphate buffered saline at pH 7.0 containing various amounts of rabbit IgG, the liquid sample flows into the hollow chamber by capillary action, where the rabbit IgG in the sample displaces some of the bound FAD conjugated monoclonal mouse anti rabbit IgG from the bound beads. These free FAD-antibodies bind to the apoglucose oxidase in the neighboring beads, creating active glucose oxidase. The resulting electrochemical reaction can then be detected. Monitoring the change in current at a 0.5 v applied potential can do this. Typical results from this type of study are shown in table 1 below.

TABLE 1

| Immunochemical assay | | | |
| --- | --- | --- | --- |
| Concentration of | Reaction time | | |
| rabbit IgG | 10 seconds | 1 minute | 2 minutes |
| 0 ug/ml IgG | 0 nA | 9 nA | 15 nA |
| 1 ug/ml IgG | 23 nA | 97 nA | 354 nA |
| 10 ug/ml IgG | 107 nA | 1.2 uA | 1.9 uA |

The sensitivity of this assay to increasing levels of rabbit IgG can be seen by the increasing amount of current as a function of time and concentration of analyte (rabbit IgG) in the applied sample.

Experiment 2

Coagulation experiment using thrombin substrate microbeads and porous electrodes. Depending upon the details of the coagulation assay or protease assay in question, many different suitable FAD-(test substrate peptide)-Anchor configurations are possible. In the specific example where the protease (proteolytic enzyme) is thrombin, a FAD-(thrombin test substrate)-anchor is desired, and the anchor is chosen to be a solid phase peptide synthesis bead, it will often be advantageous to include amino acid leader sequences on either side of the thrombin recognition and cleavage region. These leader sequences are designed to allow thrombin to get better steric access to the test substrate region, and minimize the interfering effects of both the FAD and bead on the ability of thrombin to cleave the thrombin test substrate region.

Such leader groups should thus be designed to promote steric access (allow the protease to physically reach the desired test substrate peptide), but otherwise not interfere with the reaction. Although usually some experimentation (computer modeling and/or direct synthesis of candidates) will be required to find the optimum leader combination, such leader sequences can typically be found by using the amino acid sequence that naturally brackets the protease cleavage site in the natural form of the protease substrate. For example, in the case of a coagulation assay, where it is desired to produce a thrombin test substrate analogous to the natural thrombin substrate region on human fibrinogen (see Hughes et. al., Biochemistry 2004, 43, 5246-5255, table 1), the thrombin test substrate site can be the natural fibrinogen (P3, P2, P1) sequence "G V R" (using the one letter amino acid code), bracketed on the N terminal (P6, P5, P4) side by the naturally occurring leader "E G G", and bracketed on the C terminal (P1', P2', P3') side by the naturally occurring leader "G P R". The resulting finished FAD-(peptide substrate)-Anchor will then be:

[FAD]-(E G G)-GVR-(G P R)-[peptide synthesis bead]

The apoenzyme FAD prosthetic group is [FAD], the thrombin cleavage (test substrate) site is shown underlined (GVR), and cleavage by thrombin produces the products:

[FAD]-(EGGGVR) and GPR-[peptide synthesis bead].

After thrombin cleavage, the FAD-peptide group is now liberated from the peptide synthesis bead, and is now free to diffuse over to nearby apoglucose oxidase apoenzymes and create active glucose oxidase.

In this experiment, FAD-EGGGVRGPR-beads can be created by Fmoc solid phase synthesis and FAD conjugation, suspended in the same Trehalose buffer described previously, and deposited using an air brush on the same porous Toray carbon paper electrodes along with the apoglucose oxidase microbeads as described previously. This electrode is then mounted on a solid support containing leader electrodes using the conductive adhesives described previously.

In the example where a prothrombin time coagulation test is desired, a coagulation initiator, such as a thromboplastin-calcium solution, is made up and a small (approximately 10-30 ul drop) of this solution is applied to a plastic cover. Suitable thromboplastin-calcium solutions include Dade-Behring thromboplastin C plus, Dade Innovin, Biomerieux Simplastin, and others. This thromboplastin solution is allowed to dry, creating a plastic cover with a dried thromboplastin-calcium pellet attached. This plastic cover is then laminated on top of the porous carbon electrode—support layer with a 10-30 mil thick plastic spacer, creating a lower support, porous carbon electrode, thromboplastin pellet, upper plastic support structure as shown in FIG. 8.

In use, the test strip is normally maintained at a constant physiological temperature, such as 37° C., in order to improve test accuracy. The test strip is attached to the electrochemistry measuring apparatus. When challenged with plasma or whole blood, the sample flows into the hollow chamber by capillary action, where it rehydrates the dry thromboplastin, activating the prothrombin time coagulation cascade. Thrombin, generated by the coagulation cascade, migrates into the porous carbon electrode, where it cleaves the FAD-(thrombin test substrate)-bead complex, liberating free FAD. This in turn reactivates the apoglucose oxidase, and the resulting electrochemical reaction can be detected. When used with a slow acting thromboplastin such as Dade Innovin, and the change in current at a 0.5 V applied potential is monitored, results such as table II (below) can be obtained.

TABLE II

Prothrombin time assay signal generation

| Sample type | Reaction time | | |
|---|---|---|---|
| | 30 seconds | 1 minute | 2 minutes |
| INR 1 control plasma | 2 nA | 31 nA | 97 nA |
| INR 3 control plasma | 3 nA | 3 nA | 35 nA |

Note that the INR 1 control plasma, which has a high level of coagulation factors and reacts relatively quickly, produces a significant signal by 1 minute of reaction. By contrast, the INR 3 control plasma, which has a lower level of coagulation factors and reacts much slower, takes 2 minutes to start to produce an electrochemical signal that is significantly above the background.

Other Applications:

The apoenzyme reactivation electrochemical techniques of this disclosure can also be combined with the disclosures of copending U.S. patent application Ser. Nos. 10/233,908, 10/308,411, and 10/885,429 to produce a variety of other novel and useful assays. For example, the ability of the present assay to discriminate between various types of hydrolase enzymes can be enhanced by using the steric restrictor concepts disclosed in copending application Ser. No. 10/233, 908 (incorporated herein by reference) to make the substrates shown in FIG. 1 (8), (18) more specific for particular types of hydrolase enzymes (9), (19). Thus the electrochemical detection methods of the present disclosure may be combined with the specific enzyme microarray concepts of Ser. No. 10/233, 908 to produce enzyme microarrays that are capable of simultaneously analyzing many enzymes at the same time from a sample, and reporting the results electronically via many different apoenzyme reactivation based electrodes incorporated into the microarray surface.

Figure 9:
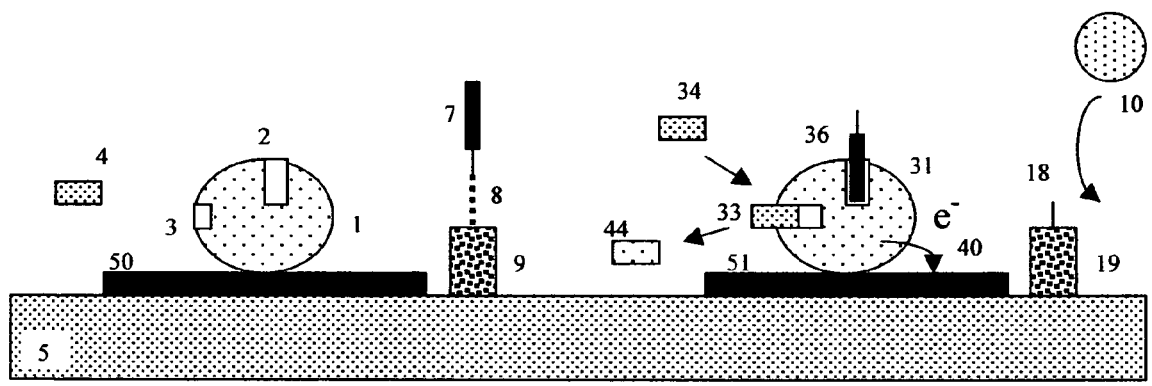
FIG. 9 shows a drawing of an apoenzyme electrochemical detection enzymatic microarray.

An example of this type of enzymatic microarray is shown in FIG. 9. FIG. 9 shows an example of a two-element electrochemical microarray, designed to be sensitive to the activity of either a first proteolytic enzyme, a second proteolytic enzyme, or both proteolytic enzymes. In this example, assume that the microarray has been constructed according to Ser. No. 10/233,908 and the present disclosure, and then has been exposed to a sample containing only an active second proteolytic enzyme (10). As previously discussed at length in copending application Ser. No. 10/233,908, incorporated herein by reference, such enzymatic microarrays, particularly microarrays composed of enhanced specificity test substrates using the steric restrictor concepts of Ser. No. 10/233,908, are potentially quite useful for analyzing clinical samples containing complex enzyme mixtures including angiogenesis assays, sepsis assays, and other types of samples.

In this diagram, apoenzymes (1, 31) are mounted or otherwise associated with the surface of two different electrodes (50, 51) mounted on solid support (5). Apoenzymes (1, 31) contain a binding site for a prosthetic group (2) (in the case of apoenzyme (31), as will be discussed; this site has been recently filled by the prosthetic group 36). Apoenzymes (1, 31) additionally contain amplification substrate-binding sites (3) (and the area immediately behind (33)). for the electrical enzyme amplification substrate (4, 34). In this example, amplification substrate (4, 34) would be glucose. Note that in the apoenzyme form of the enzyme, amplification substrate-binding site (3) will be in an inactive conformation.

In this example, the device had originally contained the FAD apoenzyme prosthetic group (7) and (36) bound to surface (5) by way of protease peptides (test substrates) (8, 18) and optional supports (9, 19). Surface (5) and optional supports (9, 19) had originally made it sterically infeasible for prosthetic groups (7 and 36) to bind to prosthetic group binding sites of apoenzymes (1 and 31). Protease peptide (8) contained a peptide region that serves as a test substrate to a first proteolytic test enzyme (not shown). Support (19) had originally contained a peptide test substrate (18) to second proteolytic test enzyme (10). However in this example, since the second proteolytic test enzyme (10) was present in the sample, it has specifically cleaved peptide test substrate (18), and as a result, the prosthetic group (36) which was originally bound to surface (5) by support (19) was free to diffuse and bind to the prosthetic group binding site of electrochemical apoenzyme 31. As a result, apoenzyme 31 has been reactivated, and now converts electrochemical enzyme amplification substrate (34) into reaction product (44) producing electrons (40), which react with electrode (51). Thus the fact that the sample contained a second test protease reactive with peptide (18) and did not contain a first test protease reactive with peptide (8) can be determined by measuring the electrical signal produced by electrodes (50) and (51).

Immunochemical devices using genetic hybrid antibody-apoenzyme proteins.

In some cases, it may be particularly advantageous to produce electrochemical antigen detection devices using hybrid antibody-apoenzyme proteins produced by genetic engineering methods. Here one or more combination (hybrid) electrochemical apoenzyme—antibody genes are constructed containing the gene of the electrically active enzyme coupled to one or more appropriate antibody immunoglobulin heavy or light chain genes. This hybrid gene can then be inserted into an antibody producing cell, virus (e.g. phage display technique), or animal, or alternatively used in a purely chemical antibody synthetic method. If the resulting fusion protein is an electrochemically active antibody-enzyme hybrid protein containing the electrochemical enzyme's prosthetic group, then this prosthetic group can be removed, converting the electrochemical enzyme into an apoenzyme, using the methods described previously.

Generally it will be advantageous to incorporate the hybrid antibody-apoenzyme genes into phages, and produce large number of variant versions of the hybrid antibody molecule, directed against different test antigens of interest, using phage display methods. Phage display methods, such as the methods disclosed in U.S. Pat. Nos. 5,223,409; 5,403,484; 5,571,698; 5,837,5001 6,660,843; etc.; are particularly advantageous because billions of alternate hybrid antibody-apoenzyme molecules can be rapidly produced and screened for both proper binding to the antigen of interest, and screened for proper function of the electrically active enzyme portion of the hybrid antibody. Those phages that produce hybrid electrically active antibodies with the desired characteristics can then be rapidly scaled-up to produce large quantities of desired hybrid antibody.

The resulting hybrid electrically active antibodies both react to antigen, and can be easily manipulated to produce an electrical response when the antibody binds to the antigen. These hybrid antibodies are particularly useful for constructing simplified electrochemical antigen detector devices.

Methods to produce electrically active antibody-enzyme hybrids:

Electrically active enzyme genes, such as the glucose oxidase gene, have previously been successfully genetically hybridized to antibody heavy chain genes, and the resulting protein has been active as both an enzyme and as an antibody. (Sznyol, Soet, Tuyl et. al. "Bactericidal effects of a fusion protein of Llama Heavy-Chain antibodies coupled to glucose oxidase in oral bacteria", Antimicrobial agents and chemotherapy September 2004, p 3390-3395, 2004.). Such coupling methods, or equivalent methods, are generally suitable for the present invention.

Figure 10:
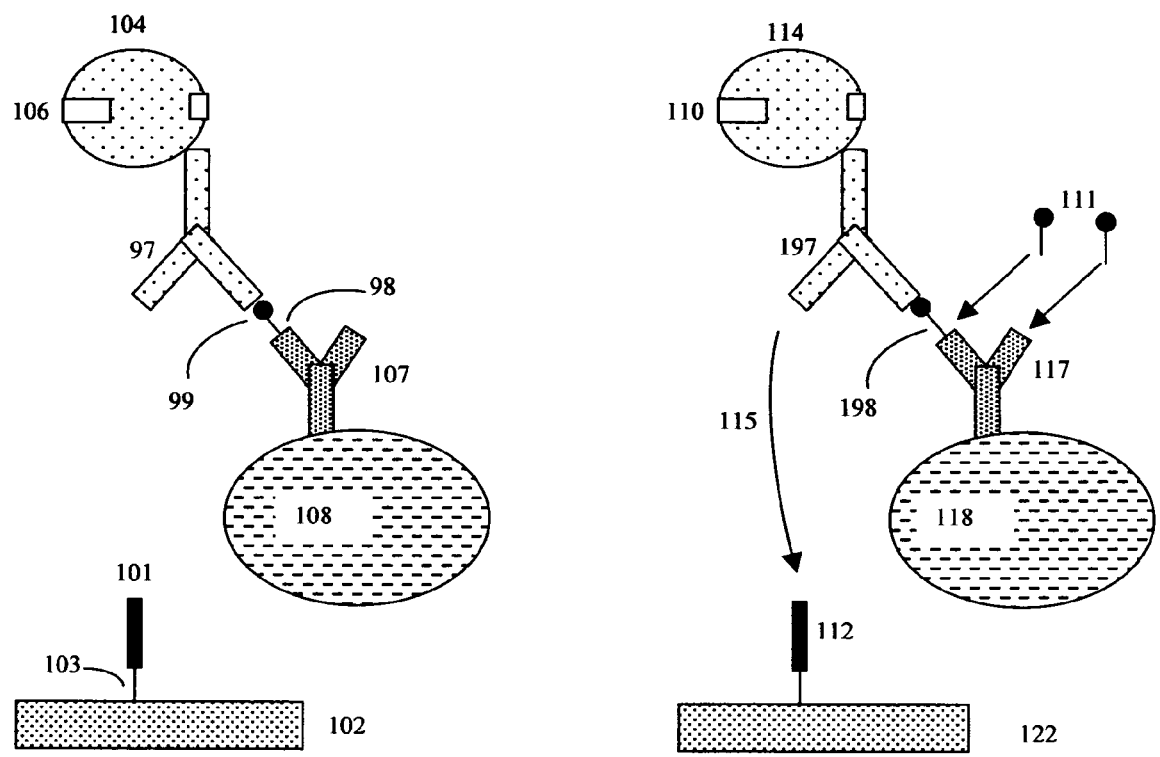
FIG. 10 shows a drawing of a single-use apoenzyme electrochemical detection immunochemical detector, using a hybrid antibody.

Such recombinant antibody-apoenzyme fusion proteins could be useful in a number of different types of electrochemical immunoassays. FIG. 10 shows a single-use sandwich immunoassay constructed using hybrid antibody-apoenzyme reagents. This sandwich immunoassay generally works according to the scheme previously described in FIG. 6. The main difference is that in FIG. 6, the apoenzyme (4), (14) contains a reagent form of the antigen (9), (19) chemically coupled to apoenzyme (4), (14), and this reagent form of the antigen (9), (19) reversibly binds to reagent antibody (7), (17) in the absence of test antigens (11). However binding of test antigens (11) displaces the apoenzyme (4), (14) from the reagent antibody, and this mobile apoenzyme can now diffuse (15) to a nearby electrode associated prosthetic group (1), (12), (21). The prosthetic group (21) reactivates the apoenzyme (24). The now reactivated enzyme converts amplification substrate (39) to product (40) producing an electrical signal (41), which is detected by electrode (32).

By contrast, in FIG. 10, hybrid antibody-apoenzyme (97)+ (104) binds to a first epitope (99) of the reagent antigen, and a second reagent antibody (107), attached to support (108, 118) binds to a second epitope (98) on the reagent antigen. This forms a sandwich that prevents the apoenzyme portion of (104) of the hybrid antibody-apoenzyme molecule from diffusing over to the prosthetic group (101) mounted by a spacer (103) (which may be an electrically conducting "wired enzyme" spacer) on or near electrode (102). The apoenzyme portion of the hybrid molecule (104) is inactive because there is no prosthetic group in the apoenzyme's prosthetic group binding site (106).

When test antigens (111) are added to the detector, these compete for binding between the antigen binding sites on the hybrid antibody-apoenzyme (114)+(197) and the tethered test antigen (198). The hybrid antibody-apoenzyme is displaced from the tethered test antigen (198) and it now can migrate (115) and bind to the nearby tethered apoenzyme prosthetic group (112) mounted on or near electrode (122). The tethered prosthetic group reactivates the apoenzyme, and the reactivated enzyme then converts amplification substrate (not shown) to product, producing an electrical signal using essentially the same scheme previously discussed in FIG. 6.

For some applications, it may be desirable to combine the present hybrid antibody-apoenzyme teaching with the tethered-ligand teachings of copending application Ser. No. 10/308,411, incorporated herein by reference, to produce a reusable immunoassay, an immunochemical microarray, or a multi-analyte antigen detection device. For these applications, it is often preferable if the enzyme portion of the antibody-enzyme hybrid is a mutant form that binds the enzyme's prosthetic group with lower affinity than the normal (wild type) form of the enzyme. This is because for reusable tethered-ligand immunoassays, it is important that the binding of the antibody to its corresponding antigen be of higher affinity than the apoenzyme's binding to the apoenzyme's prosthetic group. A number of such low affinity prosthetic group binding apoenzymes have been described in the literature. (See for example, Yamada, Inbe, Tanaka et. al., "Mutant isolation of *Escherichia coli* Quinoprotein Glucose Dehydrogenase and analysis of critical residues Asp-730 and His 775 for its function" J Biol Chem, Vol. 273, Issue 34, 22021-22027, Aug. 21, 1998.) Yamada describes a number of glucose dehydrogenase mutants (H775R and H775A) with low affinity for their prosthetic group, pyrroloquinoline quinine (PQQ). Low affinity prosthetic group binding mutants such as these are preferred for tethered-ligand immunoassays.

Figure 11:
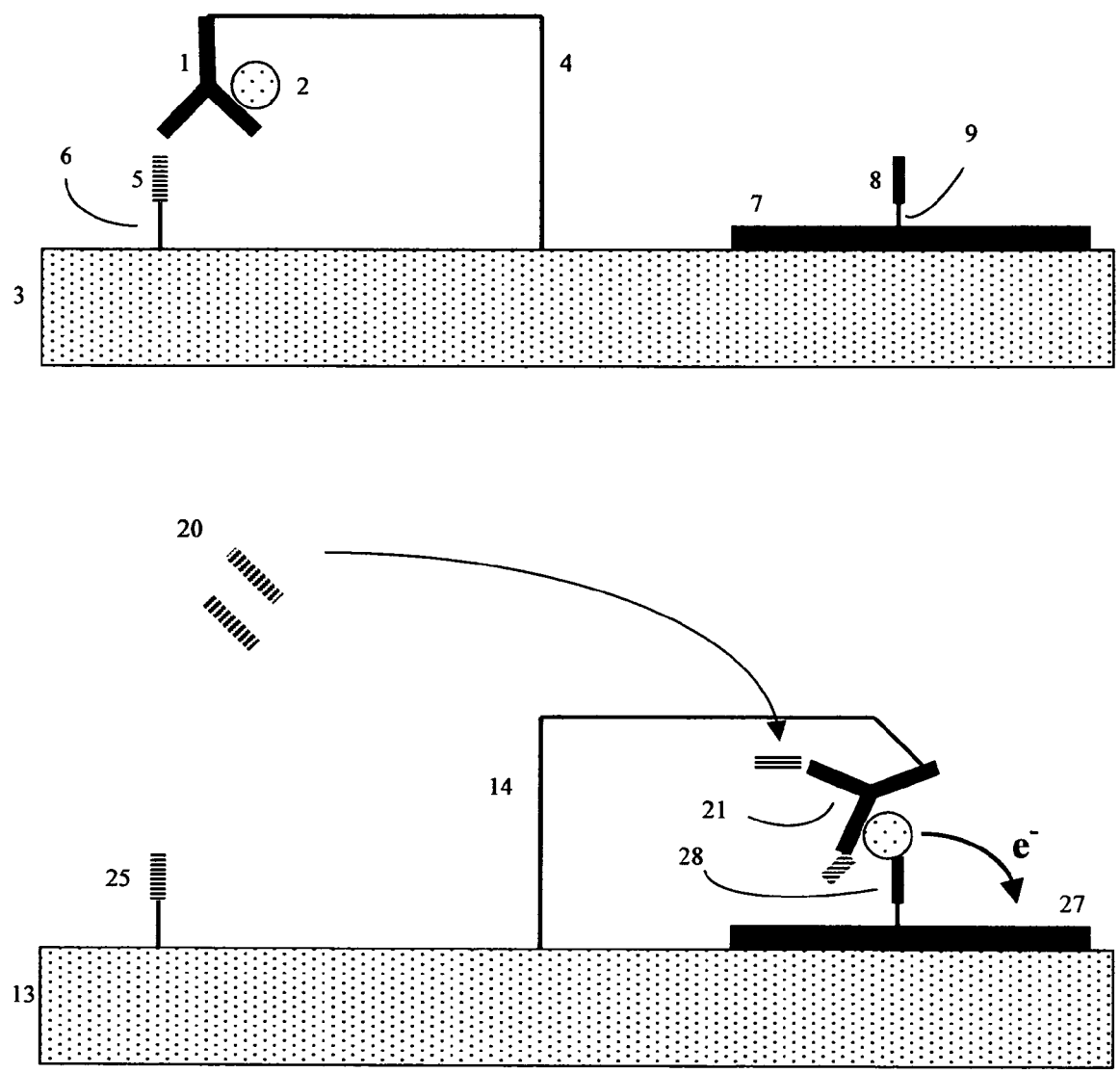
FIG. 11 shows a drawing of a reusable apoenzyme electrochemical detection immunochemical microarray, using a hybrid antibody.

In still other applications, it may be useful to screen for mutant electrical enzyme gene antibody combinations where the enzyme portion of the hybrid has an activity that is sensitive to the binding or non-binding of antigen to the antibody portion of the hybrid. Such a reusable electrochemical immunoassay is shown in FIG. 11. Here a hybrid antibody-apoenzyme molecule composed of an antibody portion (1) and an apoenzyme portion (2) is connected to a solid support (3) by the type of long hydrophilic tethers previously described in Ser. No. 10/308,411 (4). The solid support (3) additionally contains a reagent antigen (5) coupled to solid support (3) by an optional tether (6).

The solid support additionally contains an electrode (7), and an apoenzyme prosthetic group or reactivation molecule (8) connected to the support by optional tether (9). Often this optional tether may be an electrical conducting tether, capable of transmitting electrons directly from the prosthetic group (8) to electrode (7). If the affinity of apoenzyme (2) for its prosthetic group (8) is lower than the affinity of antibody (1) to its tethered antigen (5), then the hybrid antibody-apoenzyme molecule will spend the majority of its time tethered to antigen (5). The apoenzyme (2) will be in an inactive form and will not generate an electrochemical signal.

However when excess test antigens (20) are added, these compete for the antigen binding sites on antibody (1), (21). The antibody portion of the hybrid molecule detaches from tethered antigen (25). The hybrid molecule then has a much higher probability of binding to the bound prosthetic group (8) (28). As a result, the hybrid molecule now associates with the bound prosthetic group. The apoenzyme becomes reactivated, and converts its amplification substrate (not shown) to product, producing an electrochemical signal, which is detected by the electrode (7), (27).

Note that because the hybrid antibody-apoenzyme (1), (2), (21) is connected to the support (3), (13), by a flexible tether (4), (14), the test device may be washed or flushed with fresh reaction buffer (normally containing salts, a pH control buffer, and sufficient quantities of the amplification substrate for the electrically active enzyme to provide an adequate electrochemical signal for the next assay). Thus this device may be reused multiple times. An additional advantage is that because the hybrid antibody-apoenzyme and test antigen are tethered to the solid support (3), (13), and thus have a limited ability to diffuse to other areas of the device, many such detection elements may be placed onto a single support in close proximity, creating a microarray or multiple analyte detector capable of analyzing a large number of different test antigens at the same time. In some cases, it may be desirable to incorporate the device into the flow cell devices previously described in Ser. No. 10/308,411.

Invasive Diagnostic Devices

In other cases, it may be desirable to incorporate these tethered immunochemical detectors into invasive diagnostic elements designed to be incorporated into the body of a human or animal. This is possible because essentially all of the essential test components are tethered to a solid surface. The missing test ingredients—a regeneration buffer and a resuply of amplification substrate for the electrochemically active enzyme, will often be supplied by natural physiological process in the human or animals blood circulation or interstitial fluid. Thus the diagnostic test elements may be incorporated into the end of a catheter, implantable electrode, surgical tool, incorporated into a small implantable chip, or some other invasive mechanism.

If an implantable chip configuration is desired, the chip may be designed with supplemental onboard electronics to transduce the electrochemical signal into an analog or digital signal suitable for transmission outside the body. Such a signal may be transmitted over the short distance between inside and outside the body by a variety of methods, including light, infrared, or radiofrequency signals. If supplemental electrical power is needed to drive the device, the device's onboard electronics can be designed to draw power from an internal battery, from radiofrequency signals, magnetic coupling (induction) signals, or other means.

Implantable immunosensors would enable continual real time monitoring of multiple medical analytes at once, and would be suitable for many applications. In addition to monitoring for diabetes and blood circulation disorders, such implantable sensors would be well suited for monitoring sepsis or septic shock in at-risk patients, cardiovascular or kidney failure, and many other common, intensive care, medical antigen analytes.

In an alternative approach, the reusable detectors may be placed on a surgical tool designed for temporary placement into a human or animal during the course of an operation. Such invasive surgical tools may consist of human or robotic driven probes designed for either open site operations, or endoscopic (minimally invasive) small-incision surgery. Using these techniques, the probability of a surgical site to undergo thrombosis, or metastatic or angiogenic status of a tumor, etc., may be rapidly assessed. Here the signals from the detector electrodes can be relayed outside the body by either direct electrical contact (i.e. electrical wires), or through radiofrequency, light, infrared, sonic, or vibration means.

When operation inside the body is desired, the detectors should preferably be mounted on a biocompatible surface, and may additionally contain additional elements such as a porous covering (e.g. dialysis membrane, porous meshwork, hydrogel covering, etc.) designed to prolong sensor life, and retard detector biofouling.

When operation of a single use or limited lifetime use detector inside the body is desired, (either immunochemical or enzyme sensors) it may also be useful to protect the detector from initial contact with body fluids via an electrically or mechanically operated covering. One example of such an electrically operated covering is a small pore covered with a thin layer of metal or other material that, in response to a small electrical current, ruptures or opens, allowing the detector element to become exposed to body fluids. Using this technique, multiple single-use detectors can be mounted onto a biosensor or surgical tool, and progressively used to monitor analytes on an as-needed basis.

Note that although use of genetic antibody-enzyme hybrids has certain advantages, the above techniques may also be used with conventional antibody based immunochemical diagnostic devices, such as those discussed in FIGS. 2, 4, 6 of this disclosure and previously in Ser. No. 11/059,841. Alternatively the hybrid antibodies discussed in FIGS. 10 and 11 of this disclosure may be produced by chemical (non genetic) protein conjugation techniques, as described in more detail in application Ser. No. 10/308,411.

The invention claimed is:

1. An electrochemical detection device for detecting the activity of one or more hydrolase analyte enzymes in a liquid sample, said device comprising;
    at least one electrode containing an apoenzyme or otherwise inactive form of an electrochemical enzyme that, in the active form, would produce an electrochemical change in at least one of said electrodes in response to an electrochemical enzyme substrate;
    an apoenzyme cofactor, prosthetic group or other activation moiety that converts the inactive form of said electrochemical enzyme to an active form;
    said cofactor, prosthetic group or activation moiety being present in the form of at least one complex that contains at least one target substrate which is cleaved by at least one of said hydrolase analyte enzymes;
    said complex being incapable of activating the apoenzyme or otherwise inactive form of said electrochemical enzyme when said target substrate is not cleaved;
    wherein at least one of said hydrolase analyte enzymes cleaves at least one of said target substrates, enabling said cofactor, prosthetic group or said activation moiety to activate said apoenzyme or said inactive form of said electrochemical enzyme;
    resulting in a detectable electrochemical change in at least one of said electrodes; and
    wherein said complex is on a surface that is spatially separated from the region or regions of the apparatus where the apoenzyme or inactive form of said electrochemical enzyme are located.

2. The device of claim 1, in which said electrochemical apoenzyme is glucose oxidase, and the complex contains FAD as the prosthetic group or activation moiety.

3. The device of claim 1, in which said hydrolase analyte enzyme is in a liquid sample and comprises an active or inactive form of a protease, and said complex contains a protease target substrate, wherein the protease activity of said sample cleaves said target substrate, liberating said cofactor, prosthetic group or said activation moiety from said complex, resulting in activation of said electrochemical apoenzyme, and a change in the electrochemical status of said electrode.

4. The device of claim 1, in which the hydrolase analyte enzyme is selected from the group consisting of proteases (EC-3.4), esterases (EC-3.1), and glycosylases (EC-3.2).

5. The device of claim 1, in which said hydrolase analyte enzyme induced changes in the activity of said electrochemical apoenzyme is selected from the group consisting of enzyme cofactor addition, prosthetic group addition, allosteric regulator binding, covalent enzyme modification, or proteolytic cleavage.

6. The device of claim 1, in which one or more of the hydrolase analyte enzyme target substrates are enzyme target substrates for enzymes selected from the group consisting of clinical markers for coagulation, angiogenesis, inflammation, sepsis, cardiovascular status, kidney disease, kidney injury, cancer and ischemia.

7. The device of claim 1, in which the device is in the form of a disposable test strip, and in which the test strip contains integral means for producing heat to keep the device at a constant temperature during the reaction.

8. The detection device of claim 1, mounted on an invasive device selected from the group consisting of surgical tools, catheters, implantable electrodes, implantable chips, and implantable biosensors, in which the detection device is initially protected from body fluids by a removable covering.

9. The device of claim 1, in which the hydrolase analyte enzyme is a coagulation pathway protease, the target substrate that is cleaved by said hydrolase analyte enzyme is the peptide substrate to the coagulation pathway protease, and in which the device additionally contains chemical means to trigger the formation of one or more coagulation pathways in said liquid sample.

10. The device of claim 9, in which the coagulation pathway protease is thrombin, the target substrate which is cleaved by the coagulation pathway protease is a thrombin substrate, and the chemical means to trigger the formation of one or more coagulation pathways in said liquid sample comprise thromboplastin or another coagulation factor VII activating substance.

11. The electrochemical detection device of claim 1, in which the complex is connected to a solid support surface by a hydrophilic tether.

12. An immunochemical detector device for performing immunoassays for one or more test antigens, said detector comprising:
  one or more electrodes;
  one or more hybrid antibodies formed from the protein produced by a recombinant fusion hybrid between an antibody immunoglobulin gene and the gene for an electrically active enzyme;
  the enzyme protein portion of said hybrid antibodies being present in an apoenzyme or otherwise enzymatically inactive form;
  in which said apoenzyme portion or said inactive form of said hybrid antibodies, in the active form, would produce an electrochemical change in said electrode in response to an amplification substrate to the electrically active enzyme portion of the hybrid antibody;
  said device additionally containing an apoenzyme cofactor, prosthetic group, or other activation moiety that converts the enzymatically inactive form of said hybrid antibody to an enzymatically active form;
  said hybrid antibody or said cofactor or activation moiety being present in the form of a complex that changes its structure due to interactions with a test antigen in a test sample;
  wherein said test antigen induces changes in said complex, enabling said cofactor, prosthetic group or said activation moiety to activate said enzymatically inactive hybrid antibody, resulting in a detectable electrochemical change in one or more of said electrodes.

13. The immunochemical detector device of claim 12, in which said gene for said electrically active enzyme is a gene for a mutant form of said electrically active enzyme with an affinity for the enzyme's cofactor or prosthetic group that is lower than that of the wild type gene's affinity for the enzyme's cofactor or prosthetic group.

14. The immunochemical detector device of claim 12, in which said one or more of said hybrid antibodies are produced by phage display technology using recombinant genes composed of fused antibody immunoglobulin genes and electrically active enzyme genes.

15. The immunochemical detector device of claim 12, in which the test antigen is selected from the group consisting of markers for sepsis, angiogenesis, pregnancy, ovulation, cardiovascular status, infectious disease, drugs of abuse, therapeutic drugs, kidney disease, ischemia, coagulation and cancer diagnostics.

16. The immunochemical detector device of claim 12, in which the test antigen is selected from the group of consisting of markers for calcitonin, procalcitonin, c-reactive protein, endogenous activated protein C, tumor necrosis factor, interleukin-6, interleukin 10, endotoxin, lipopolysacharide binding protein, pro-atrial natriuretic peptide, C difficile, Hepatitis, HIV, influenza, legionelly, pneumonia, RSV, strep, syphilis, early pregnancy factor, human chorionic gonadotropin, luteinising hormone, amphetamines, barbiturates, benzodiazepines, cocaine, methamphetamines, opiates, phencyclidine, THC, trycyclic antidepressants, acetaminophen, carbamazepine, phenytoin, theophylline, drotrecogin alfa, tissue plasminogen activator, cystantin C, neutrophil gelatinase-associated lipocalin, interleukin-18, kidney injury molecule-1, proatrialnatriuretic peptide, d-dimer, troponin I, CKMB, myoglobin, nt Pro BNP, ischemia modified albumin, myeloperoxidase, S-100 beta, and prostate specific antigen.

17. The immunochemical detector device of claim 12, mounted on a device selected from the group consisting of surgical tools, catheters, implantable electrodes, implantable chips, and implantable biosensors.

18. The immunochemical detector device of claim 12, mounted on an implantable biosensor, in which the biosensor contains electronic means to transmit signals from said detector outside the body, said means selected from the group consisting of radiofrequency signals, light signals, infrared signals, sonic signals, and vibration signals.

19. The immunochemical detector device of claim 12, in which the complex is connected to a solid support surface by a hydrophilic tether.

20. A method for detecting the activity of one or more hydrolase analyte enzymes in a liquid sample, said method comprising;
  obtaining a device comprising at least one electrode containing an apoenzyme or otherwise inactive form of an electrochemical enzyme that, in the active form, would produce an electrochemical change in at least one of said electrodes in response to an electrochemical enzyme substrate;
  an apoenzyme cofactor, prosthetic group or other activation moiety that converts the inactive form of said electrochemical enzyme to an active form;
  said cofactor, prosthetic group or activation moiety being present in the form of at least one complex that that contains at least one target substrate which is cleaved by at least one of said hydrolase analyte enzymes;
    said complex being incapable of activating the apoenzyme or otherwise inactive form of said electrochemical enzyme when said target substrate is not cleaved;
    wherein at least one of said hydrolase analyte enzyme cleaves at least one of said target substrates, enabling said cofactor, prosthetic group or said activation moiety to activate said apoenzyme or said inactive form of said electrochemical enzyme; resulting in a detectable electrochemical change in at least one of said electrodes;
    in which one or more hydrolase analyte enzymes is added to the device, the electrochemical status of various device electrodes is assessed, and the relative activity of the various hydrolase analyte enzymes present in the sample is determined; and
    wherein said method is used to analyze the status of a coagulation pathway, in which the hydrolase analyte enzyme is a coagulation pathway protease, the target substrate which is cleaved by said hydrolase analyte enzyme is the peptide substrate to the coagulation pathway protease, and in which the device additionally contains chemical means to trigger the formation of one or more coagulation pathways in said liquid sample.

* * * * *